United States Patent
Gray et al.

(10) Patent No.: US 8,262,634 B1
(45) Date of Patent: Sep. 11, 2012

(54) ABSORBENT ARTICLE HAVING BARRIER SHEET AGAINST THE MIGRATION OF THE SKIN CARE COMPOSITION

(75) Inventors: Brian Francis Gray, Cincinnati, OH (US); Kiyoe Ohba, Fukuoka Fukuoka (JP); Ryo Minoguchi, Cincinnati, OH (US); Kaoru Niihara, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/089,338

(22) PCT Filed: Oct. 1, 1999

(86) PCT No.: PCT/US99/22843
§ 371 (c)(1),
(2), (4) Date: Jan. 17, 2003

(87) PCT Pub. No.: WO01/24748
PCT Pub. Date: Apr. 12, 2001

(51) Int. Cl.
*A61F 13/15* (2006.01)

(52) U.S. Cl. .............. 604/385.05; 604/364; 604/385.04; 424/443

(58) Field of Classification Search ............. 604/385.02, 604/385.05, 385.04, 364; 424/402, 443, 424/403
See application file for complete search history.

(56) References Cited

U.S. PATENT DOCUMENTS

| | | | | |
|---|---|---|---|---|
| 4,687,478 A * | 8/1987 | Van Tillburg | | 604/387 |
| 4,959,059 A * | 9/1990 | Eilender et al. | | 604/358 |
| 5,019,064 A * | 5/1991 | Eilender | | 604/378 |
| 5,643,588 A | 7/1997 | Roe et al. | | |
| 5,683,377 A * | 11/1997 | Mizutani | | 604/390 |
| 5,720,739 A * | 2/1998 | Hilston et al. | | 604/390 |
| 6,074,376 A * | 6/2000 | Mills | | 604/390 |
| 6,312,417 B1 * | 11/2001 | Hansson | | 604/385.02 |
| 6,497,692 B1 * | 12/2002 | Tameishi et al. | | 604/385.02 |
| 6,656,168 B2 * | 12/2003 | Braverman et al. | | 604/308 |
| 6,783,519 B2 * | 8/2004 | Samuelsson | | 604/385.05 |
| 2004/0243084 A1 * | 12/2004 | Yoshimasa et al. | | 604/385.01 |
| 2005/0137554 A1 * | 6/2005 | Mizutani et al. | | 604/385.02 |

FOREIGN PATENT DOCUMENTS

| | | |
|---|---|---|
| EP | 0 347 319 A1 | 12/1989 |
| GB | 2 306 428 A | 5/1997 |
| GB | 2311727 A * | 8/1997 |
| JP | 04-12013 | 4/1992 |
| JP | H08-047506 | 2/1996 |
| JP | H09-087405 | 3/1997 |
| WO | WO 98/42285 A1 | 10/1998 |
| WO | WO 98/42286 A1 | 10/1998 |
| WO | WO 9842286 A1 * | 10/1998 |

OTHER PUBLICATIONS

English language abstract for JP 04-120138 A to Tsuchiya, published Apr. 21, 1992.*

* cited by examiner

*Primary Examiner* — Melanie Hand
(74) *Attorney, Agent, or Firm* — Andres E. Velarde

(57) ABSTRACT

An absorbent article having a barrier sheet against a skin care composition is disclosed. The absorbent article has a body surface and a garment surface. The absorbent article comprises an absorbent core. At least a portion of the absorbent article has a skin care composition provided thereon. The absorbent article has a barrier sheet. The barrier sheet is treated to reduce the migration of the skin care composition therethrough.

6 Claims, 7 Drawing Sheets

ABSORBENT ARTICLE HAVING BARRIER SHEET AGAINST THE MIGRATION OF THE SKIN CARE COMPOSITION

TECHNICAL FIELD

This application relates to absorbent articles including, but not limited to, feminine hygiene garments such as sanitary napkins and panti-liners, diapers, training pants, adult incontinence devices, diaper holders, and the like. More particularly, the present invention relates to absorbent articles having a skin care composition.

BACKGROUND OF THE INVENTION

All manner and variety of absorbent articles configured for the absorption of body fluids such as menses, urine and feces are, of course, well known. With respect to feminine barrier devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986. Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is FRESH 'N FIT® PADETTE interlabial product which is marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

Although these products such as sanitary napkins, tampons and interlabial pads are effective generally to absorb menses, there are still discomfort which need to be solved. For example, the wearer feels uncomfortable due to; (1) frictional discomfort associated with rubbing of the product against the wearer's skin while wearing/applying the product; (2) adherence of the menses discharged onto the topsheet to the wearer's skin; and (3) adherence of the surface of the product such as a topsheet to the wearer's skin. The friction when applying the product prevents the product from being properly inserted/applied, leading to discomfort. In addition, rubbing of the product against the wearer's skin causes itch and/or skin irritation. The adherence of the menses gives the wearer messy/dirty feeling. In addition, enzyme and/or microbial contained in the adhered menses attack the wearer's skin, thereby causing itch and/or skin irritation. The adherence of the topsheet gives the wearer sticky feeling. It also hinders the wearer's skin from air circulation, thereby causing skin overhydration.

Thus, it would be desirable to apply compositions on absorbent articles, which have an effect to reduce wearer's discomfort associated with wearing absorbent articles. One composition which is known to reduce wearer's discomfort is an oil-based composition. The oil-based composition is known to have an effect to soften, smoothen, coat, moisturize, lubricate, or cleanse the skin. The oil-based composition is also known to have an effect to reduce wetting of the sweat, feces, and/or menses against the skin and/or the topsheet of the article. However, such an oil-based composition tends not to remain localized on the surface of the absorbent article. Instead, it tends to migrate to other portions of the absorbent article by a direct contact or through packaging or a wrapper material of the absorbent article. If the oil-based composition migrates to an unexpected portion of the absorbent article, the oil-based composition tends to degrade the quality of the portion of the absorbent article. For example, if the oil-based composition migrates to a portion of the topsheet where the oil-based composition is not intended to be applied, the overall liquid absorbency of the absorbent article through the topsheet may reduce. Further, if the oil-based composition migrates toward an adhesive used to construct the absorbent article, and/or an adhesive used to secure a portion the absorbent article to other articles such as a wearer's undergarment, the adhesive may be degraded by a contact with the oil-based composition. As a result, the absorbent article may deconstruct or the adhesive of the absorbent article may not work as expected.

Thus, there is a need for an absorbent article to reduce the migration of a composition which has an effect to reduce wearer's discomfort associated with wearing absorbent articles.

SUMMARY OF THE INVENTION

The present invention relates to an absorbent article having a barrier sheet. The absorbent article has a body surface and a garment surface. The absorbent article comprises an absorbent core. At least a portion of the absorbent article has a skin care composition provided thereon. The absorbent article has a barrier sheet. The barrier sheet is treated to reduce the migration of the skin care composition therethrough.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
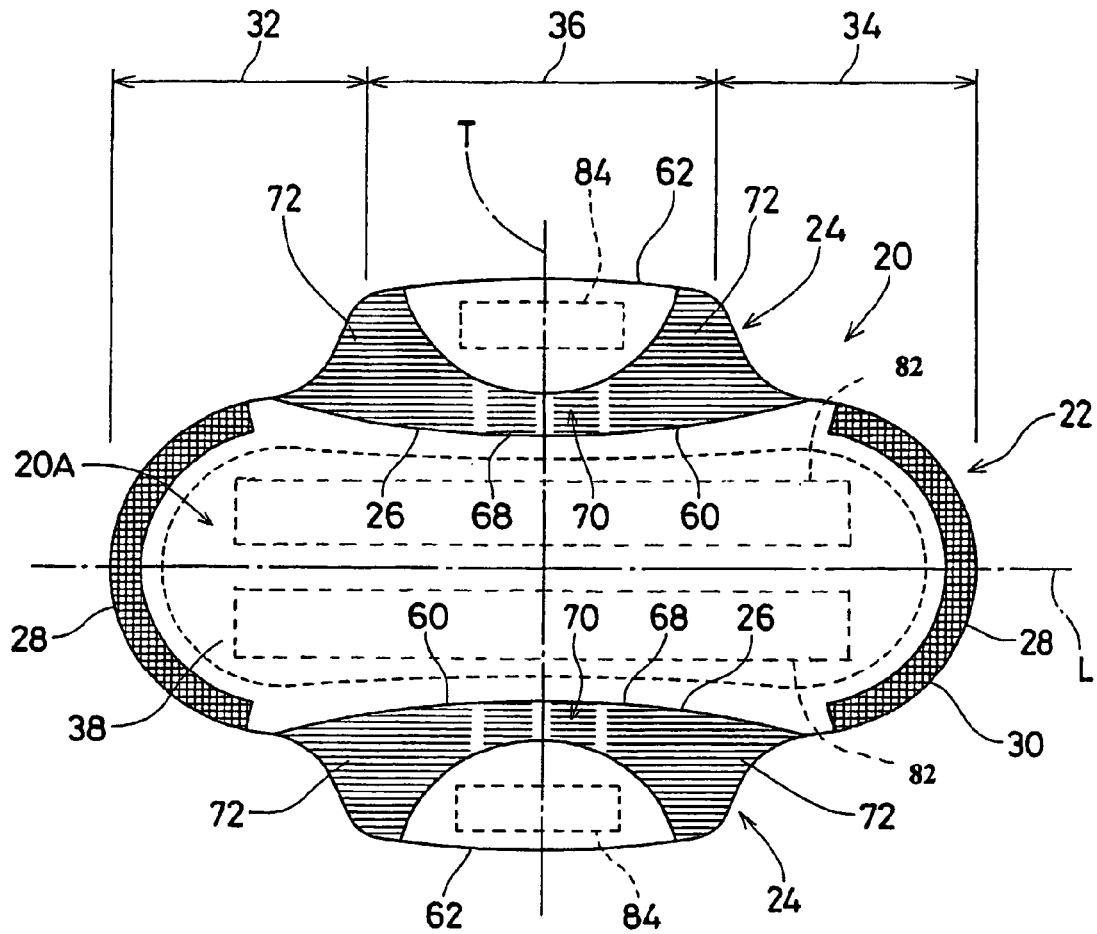
FIG. 1 is a top plan view of one embodiment of an absorbent article in the form of a sanitary napkin.

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of".

All percentages, ratios and proportions used herein are by weight unless otherwise specified.

A. Absorbent Article

Herein "absorbent article" refers to devices which absorb and contain body exudates, and more specifically, refers to devices which are placed against the skin of a wearer to absorb and contain the various exudates discharged from the body. Herein "disposable" is used to describe absorbent articles which are not intended to be laundered or otherwise restored or reused as an absorbent article after a single use. Examples of disposable absorbent articles include feminine hygiene garments such as sanitary napkins and panti-liners, diapers, incontinence briefs, diaper holders, training pants, and the like.

Disposable absorbent articles typically comprise a liquid pervious topsheet, a liquid impervious backsheet joined to the topsheet and an absorbent core positioned between the topsheet and the backsheet. Disposable absorbent articles and components thereof, including the topsheet, backsheet, absorbent core, and any individual layers of these components, have a body surface and a garment surface. Herein "body surface" means that surface of the article or component which is intended to be worn toward or adjacent to the body of the wearer, while the "garment surface" is on the opposite side and is intended to be worn toward or placed adjacent to the wearer's body or undergarments when the disposable absorbent article is worn.

As used herein, the term "body contacting surface" of an absorbent article is one or more surfaces of any article components that contact the wearer at some time during the wear period. Body contacting surfaces include, but are not limited to, portions of the topsheet, flaps, leg cuffs, waist region, side panels, fastening tabs, etc., which contact a wearer during use.

The following description generally discusses the absorbent core, topsheet, and backsheet materials that are useful in disposable absorbent articles, though disposable absorbent article does not necessarily need to have all of them. It is to be understood that this general description applies to these components of the specific absorbent articles shown in FIGS. 1-3 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). The absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g.; wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. Herein "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet may be embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment means such as those well known in the art. However, embodiments of the present invention are envisioned wherein portions of the entire absorbent core are unattached to either the topsheet, the backsheet, or both.

For example, the topsheet and/or backsheet can be joined to the absorbent core or to each other in any suitable manner known in the art. The term "joined", as used in this specification, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The backsheet and/or the topsheet may be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Skin care compositions are applied to at least a portion of the body contacting surface of the absorbent article. The skin care composition may be applied to a portion of or the entirety of the body contacting surface. It is preferable to apply the skin care composition to the entirety of the body contacting surface. Further, the skin care composition may be applied to the garment surface of the absorbent article if desired. The skin care composition may be applied in any suitable configuration, such as a plurality of stripes, a plurality of wave lines, a plurality of dots, etc. Typically, the skin care composition is oil-based. Herein, the term "oil-based" means substantially free of water. Details of the skin care compositions are described below.

A barrier sheet is provided to the absorbent article. A barrier sheet is treated to reduce the migration of the skin care composition through the barrier sheet. Preferably, the barrier sheet substantially prevents the migration of the skin care composition through the barrier sheet. More preferably, the barrier sheet completely prevents the migration of the skin care composition through the barrier sheet. Herein, the term "migrate", "migration", or "migrating" mean the skin care composition moves from one place to another place by way of, such as a direct contact or a permeation through an intervening material. Herein, the term "substantially prevent" means that a barrier sheet prevents the migration of substantial amount of a skin care composition through the barrier sheet. The prevention level (i.e., durability effect) of the barrier sheet against the skin care composition can be measured by Accelerated Migration Test. The Accelerated Migration Test includes the following steps; (1) lay 120×120 mm of a test material (i.e., barrier sheet) on 120×120 mm of a powder paper supplied by Daishowa Paper Manufacturing Co. Ltd., 4-1-1, Imai, Fuji, Shizuoka, 417, Japan, (2) put these two sheets on a transparent plastic petri dish made by Becton Dickson and Company under the name Falcon Disposable Petri Dish 1005 having a diameter of 100 mm, so that the test material faces upwardly, (3) put the skin care composition molded into 12 mm of diameter×4 mm of thickness on the center of the test material, (4) put the lid of the plastic petri dish while pulling the four ends of the sheets so that there is no apparent space between the test material and the powder paper, whereby Migration Test Sample is complete, (5) hold the Migration Test Sample in an incubator at 40±1° C., and (6) observe a visible oil stain on the powder paper by a normal naked eye from the bottom of the petri dish with a distance of 10 cm every 2 hours. If a visible oil stain on the powder paper is observed at the time of observation, it is assessed that the migration of a skin care composition through a barrier sheet has occurred and a barrier sheet has a durability effect under the accelerated condition to prevent the migration of the skin care composition through the barrier sheet up to the time of the last observation. A barrier sheer preferably has a durability effect of 12 hours under the accelerated condition, more preferably a durability effect of 24 hours under the accelerated condition, most preferably a durability effect of 48 hours under the accelerated condition. Details of the barrier sheet are described below.

The barrier sheet may be disposed to directly or indirectly cover a portion of the absorbent article which is not desired to be exposed to the skin care composition. The barrier sheet reduces, preferably substantially prevents the migration of the skin care composition through the barrier sheet toward the portion of the absorbent article. For example, the barrier sheet may cover a portion of the absorbent article, such as an adhesive to join elements of the absorbent article to construct the absorbent article, an adhesive to secure the absorbent article to the wearer's body or the wearer's undergarment, a portion of the topsheet of the absorbent article which is not desired to be provided with the skin care composition, or a portion of the backsheet of the absorbent article which is not desired to be provided with the skin care composition.

The barrier sheet may be disposed to directly or indirectly cover a portion of the absorbent article which is provided with the skin care composition. The barrier sheet reduces, preferably substantially prevents the migration of the skin care composition from the portion of the absorbent article which is provided with the skin care composition through the barrier sheet toward, e.g., other portions of the absorbent article, portions of other different absorbent articles, or portions of other different articles. For example, the barrier sheet may cover a portion of the absorbent article which is provided with the skin care composition such as a topsheet, or may cover and wrap the entirety of the absorbent article.

The barrier sheet may be used for an element of the absorbent article such as a topsheet or a backsheet. If the barrier sheet is used for a topsheet, the topsheet helps reduce the migration of the skin care composition which is provided on the topsheet through the topsheet into the absorbent core. If the barrier sheet is used for a backsheet, the backsheet helps reduce the migration of the skin care composition through the backsheet.

A preferred embodiment of an absorbent article is shown in FIG. 1. Shown in FIG. 1 is a sanitary napkin which is one type of feminine barrier devices and is used for external wear about the pudendal region of the wearer. As shown in FIG. 1, the sanitary napkin 20 preferably comprises an absorbent means (or "main body portion") 22, and two optional flaps 24. The sanitary napkin 20 has two surfaces, a body-facing surface or "body surface" or and a garment surface 20B. The sanitary napkin 20 is shown in FIG. 1 as viewed from its body surface 20A. The body surface 20A is intended to be worn adjacent to the wearer's body. The garment surface 20B is intended to be placed adjacent to the wearer's undergarments when the sanitary napkin 20 is worn. In the embodiment shown in FIG. 1, "body contacting surface" includes the body surface 20A.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 also has two end regions, which are designated first end region 32 and second end region 34. A central region 36 is disposed between the end regions 32 and 34. The end regions 32 and 34 extend outwardly in the longitudinal direction from the edges of the central region 36 about ⅛ to about ⅓ of the length of the main body portion. A detailed description of the characteristics of a central region and two end regions for a sanitary napkin is contained in U.S. Pat. No. 4,690,680 issued to Higgins on Sep. 1, 1987.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of an ultra-thin sanitary napkin. The main body portion 22 of the sanitary napkin 20 may also be relatively flexible, so that it is comfortable for the wearer. It should, however, be understood that the sanitary napkin shown is merely one embodiment, and that the present invention is not limited to absorbent articles of the type or having the specific configurations shown in the drawings.

Figure 2:
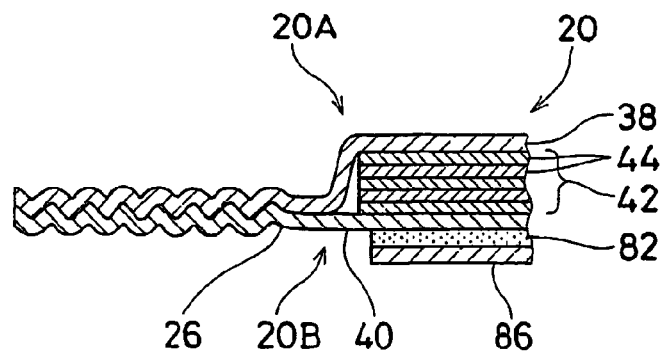
FIG. 2 is a lateral cross-sectional view taken along line 2-2 of the sanitary napkin shown in FIG. 1.

FIG. 2 shows the individual components of the main body portion 22 of the sanitary napkin 20. The main body portion 22 of the sanitary napkin 20 preferably comprises at least three primary components. These include a liquid pervious topsheet 38, a liquid impervious backsheet 40, and an absorbent core 42 positioned between the topsheet 38 and the backsheet 40. Optionally, the absorbent core 42 may include other components such as an acquisition component 44. The acquisition component 44 may either be a separate component positioned between the topsheet 38 and the absorbent core 42, or it may comprise part of a composite topsheet or part of the absorbent core 42.

A topsheet 38 which is particularly suitable for use in the sanitary napkin 20 comprises an apertured formed film. Apertured formed films are preferred for the topsheet because they are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; U.S. Pat. No. 4,780,352 entitled "Covering Structure For Absorbent Hygienic Sanitary Products, and an Absorbent Product Having Such A Covering", which issued to Palumbo on Oct. 25, 1988; U.S. Pat. No. 5,006,394 "Multilayer Polymeric Film" issued to Baird on Apr. 9, 1991; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996).

In a preferred embodiment, the topsheet 38 comprises an apertured formed film made in accordance with U.S. Pat. Nos. 4,342,314 issued to Radel, et al. and 4,463,045 issued to Ahr, et al., which is marketed on sanitary napkins as the DRI-WEAVE topsheet by The Procter & Gamble Company of Cincinnati, Ohio. Such an apertured film is preferably obtained as product No. X-5652 from Tredegar Film Products of Terre Haute, Ind. In this preferred embodiment, during manufacture the resin used to form the apertured film is preferably provided with a surfactant incorporated therein.

In preferred embodiments of the present invention, the body surface of the topsheet 38 is hydrophilic so that liquids will be transferred through the topsheet more readily. If the topsheet is made of a hydrophobic material, at least the upper surface of the topsheet is treated to be hydrophilic so that liquids will transfer through the topsheet more rapidly. This diminishes the likelihood that menstrual fluid will flow off the topsheet rather than flowing into and being absorbed by the absorbent core. The body surface of the topsheet 38 can be made hydrophilic by treating it with a surfactant. Suitable methods of treating a topsheet with a surfactant are described in U.S. Pat. No. 4,950,254 issued to Osborn; U.S. Pat. No. 4,988,344 entitled "Absorbent Articles with Multiple Layer Absorbent Layers" issued to Reising, et al on Jan. 29, 1991; and U.S. Pat. No. 4,988,345 entitled "Absorbent Articles with Rapid Acquiring Absorbent Cores" issued to Reising on Jan. 29, 1991.

A backsheet 40 which is particularly suitable for use in the sanitary napkin 20 comprises a polyethylene film having a thickness of from about 0.012 mm (0.5 mil) to about 0.051 mm (2.0 mils) as stated above. A suitable backsheet material is obtained as product No. 18-1401 from the Clopay Corporation of Cincinnati, Ohio. A suitable breathable backsheet material is a laminate of an apertured film such as that described in U.S. Pat. No. 3,929,135 issued to Thompson which is inverted so that the smaller openings of the tapered capillaries face the absorbent core 42 which is adhesively laminated to a microporous film such as that described in Exxon's U.S. Pat. No. 4,777,073.

An absorbent core 42 which is particularly suitable for use in the sanitary napkin 20 comprises a multi-bonded air laid nonwoven material. In this preferred embodiment, this multi-bonded air laid nonwoven material comprises about 52% cellulose fibers, about 20% bi-component fibers, about 25% superabsorbent hydrogel-forming material (or absorbent gelling material) particles, and about 3% latex binder. The absorbent core 42 preferably has a basis weight of about 125 g/yd$^2$ (about 150 g/m$^2$), including the particles of absorbent gelling material. Preferably, this multi-bonded air laid nonwoven absorbent core 42 is formed by depositing three streams of cellulose and bi-component fibers, with absorbent gelling material particles 58 laid down with the last stream of fibers to form the bottom portion of the absorbent core. While the absorbent core 42 is shown as a laminate in FIGS. 2 and 3, in preferred embodiments, the fibers are blended together to form a single web. Such a multi-bonded air laid nonwoven material is preferably obtained in roll form as product 915000X313 from Merfin Hygienic Products.

In alternative embodiments, the multi-bonded air laid nonwoven material used for the absorbent core can be bonded using some material other than latex (such as starch or PVA, for example). In another alternative embodiment, the absorbent core can be formed as a laminate that preferably also has a basis weight of about 150 g/m$^2$ and comprises two (or more) layers of multi-bonded air laid nonwoven material with the particles of absorbent gelling material therebetween. Suitable laminate absorbent core structures are described generally in U.S. Pat. Nos. 4,950,264 and 5,009,653 issued to Osborn, U.S. Pat. No. 5,460,623 issued to Emenaker, et al. Another suitable absorbent core is described in U.S. patent application Ser. No. 08/122,114, entitled "Sanitary Napkin Having Core Predisposed To A Convex Upward Configuration", filed in the name of Hines, et al. on Sep. 16, 1993 (PCT Publication No. WO 95/07674, published Mar. 23, 1995).

In the case of thicker sanitary napkins, the absorbent core 42 is preferably comprised of airfelt. Suitable absorbent cores for thicker sanitary napkins are described in U.S. Pat. No. 5,234,422 issued to Sneller, et al. In a preferred embodiment, the topsheet 38, acquisition component 44, and absorbent core 42 can be provided with embossed channels as shown in the Sneller, et al. patent. If such embossed channels are used, they preferably lie laterally outside of the longitudinally-oriented concave lines 56A defining the sides of the unbonded window 54.

The absorbent core 42 optionally includes an acquisition component 44. The acquisition component 44 can be made from any materials suitable. The acquisition component 44 may, for example, be comprised of woven or nonwoven materials. The fibers or other components of these materials may be synthetic, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers. The acquisition component 44 may also be at least partially comprised of cross-linked cellulose fibers. The acquisition component 44, if nonwoven, can be made by a number of different processes. These include, but are not limited to: air laid, wet laid, meltblown, spunbonded, carded, thermally bonded, air-through bonded, powder bonded, latex bonded, solvent bonded, spunlaced, and combinations of the foregoing.

An acquisition component 44 which is particularly suitable for use in the sanitary napkin 20 comprises a laminate of two nonwoven materials. The uppermost layer preferably comprises an 19 g/yd$^2$ (22.5 g/m$^2$) spunbonded polypropylene nonwoven material referred to as product No. 065MLPV60U (or "P-9") obtained from Fiberweb, North America of Washougal, Wash. The underlying layer preferably comprises a multi-bonded air laid nonwoven material that is thermally bonded using powder bonding and latex bonding. In a preferred embodiment, this multi-bonded air laid nonwoven material comprises about 77% cellulose fibers, about 20% powder binder, and about 3% latex binder (1.5% sprayed on each side of the web) and has a basis weight of about 50 g/yd$^2$ (about 60 g/m$^2$). Such a multi-bonded air laid nonwoven is preferably obtained as product No. 90830X312 from Merlin Hygienic Products, Ltd. of Delta, British Columbia, Canada. These two nonwoven layers are preferably laminated together by depositing the multi-bonded air laid nonwoven material on the spunbonded polypropylene nonwoven material. The spunbonded material is used as a process aid or carrier web in the process of forming this laminate.

In alternative embodiments, the spunbonded polypropylene nonwoven material may have a greater or a lower basis weight, or it may be replaced by an air laid tissue, a wet laid tissue, or any of the materials described above. If a wet laid tissue is used instead of a polypropylene nonwoven material, the orientation of the laminate is preferably reversed so that in the finished product, the multi-bonded air laid nonwoven material lies above the wet laid tissue layer. In the case of thicker sanitary napkins, any of the acquisition components described above can be used. Additionally, in one preferred thicker sanitary napkin embodiment, a low density latex bonded air laid material can be used as the entire acquisition component (that is, no tertiary topsheet is required). A low density latex bonded air laid material suitable for this purpose is a material having a basis weight of about 80 g/m$^2$ known as product No. FG413 MHB, which is obtained from Walkisoft, USA of Mt. Holly, N.C.

Figure 3:
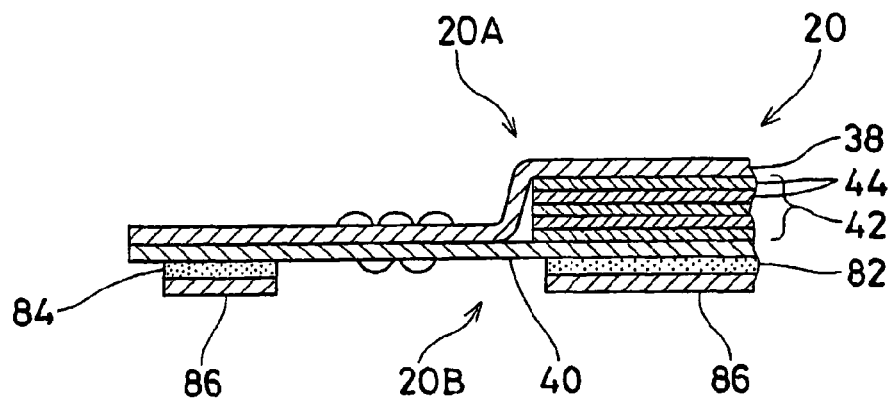
FIG. 3 is a lateral cross-sectional view taken along line 3-3 of FIG. 1 through the center portion of one of the flaps.

The topsheet 38, the backsheet 40, and the absorbent core 42 may be assembled in a variety of configurations known in the art (including layered or "sandwich" configurations and wrapped or "tube" configurations). FIGS. 1-3 show a preferred embodiment of the sanitary napkin 20 assembled in a sandwich construction. In FIGS. 1-3, the topsheet 38 and the backsheet 40 have length and width dimensions generally larger than those of the absorbent core 42. The topsheet 38 and the backsheet 40 extend beyond the edges of the absorbent core 42 to form portions of the periphery 30. In the embodiment shown in FIGS. 2 and 3 having the acquisition component 44, the garment-facing side of the topsheet 38 is preferably joined to the body-facing side of the absorbent core (i.e., the body-facing side of the acquisition component 44). If the absorbent core 42 has a layered structure, each layer may be joined each other, if desired. The acquisition component 44 may be joined to the absorbent core 42, if desired. If these components are joined, they can be joined in any of the manners described hereinabove. The backsheet 40 is preferably joined to the garment-facing side of the absorbent core 42 by adhesives.

The portions of the topsheet 38 and backsheet 40 that extend beyond the edges of the absorbent core 42 are preferably also joined to each other. Preferably, in the embodiment shown, these portions of the topsheet 38 and backsheet 40 are joined using adhesives over substantially the entire portions that extend beyond the edges of the absorbent core 42 and a crimp seal at the end edges 28 of the main body portion 22 where the topsheet 38 and backsheet 40 are densified by the application of pressure or heat and pressure.

The sanitary napkin 20 shown in FIGS. 1-3, as discussed above, comprises an optional pair of flaps 24 that are joined to the main body portion 22. The flaps 24 extend laterally outward beyond the longitudinal side edges 26 of the main body portion 22 from their proximal edges 60 to their distal edges (or "free end") 62. The flaps 24 extend outward from at least the central region 36 of the main body portion 22.

The flaps 24 can be joined to the main body portion 22 in any suitable manner. Preferably, in the embodiment shown in FIGS. 1-3, the flaps 24 are integral with the main body portion 22 (that is, the flaps 24 comprise integral extensions of the topsheet 38 and backsheet 40). In other alternative embodiments, the flaps 24 can comprise separate components that are joined to the main body portion 22. The flaps 24 are each joined to (or associated with) main body portion 22 along a juncture. This is typically a longitudinally-oriented (or "longitudinal") juncture, such as lines of juncture 68. As used herein, the terms "juncture" (or "line of juncture") refer to regions where the flaps 24 extend from or are joined to the main body portion 22. The line of juncture 68 in the embodiment illustrated in the drawings can be considered to be defined by concave inwardly-oriented regions or lines. When the sanitary napkin 20 is worn by the wearer, the flaps 24 are folded under the wearer's undergarment. The flaps 24 are typically folded along or adjacent the proximal edges 60. If the width of crotch of wearer's undergarment is narrower than that of the main body portion 22, the flaps 24 may be folded along a longitudinal portion of the main body portion 22 inside the proximal edge 60. If the width of crotch of wearer's undergarment is wider than that of the main body portion 22, the flaps 24 may be folded along a hinge 70 of the main body portion 22 which is described below.

The sanitary napkin may have first flaps (front flaps) and second flaps (back flaps). The first flap is shifted toward the one end edge (front edge) of the sanitary napkin from the transverse center line of the sanitary napkin. The first flap is folded over the topsheet before use of the sanitary napkin. The second flap is shifted toward the other end edge (back edge) of the sanitary napkin from the transverse center line of the sanitary napkin. The second flap is folded over the topsheet before use of the sanitary napkin. When the sanitary napkin is used, the first flap is folded to wrap the crotch region of the wearer's undergarment and the second flap is widespread at the back region of the wearer's undergarment.

The flaps 24 can be in any suitable configuration. Suitable flaps are described in Reexamined U.S. Pat. No. 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,389,094 entitled "Absorbent Article Having Flaps and Zones of Differential Extensibility" issued to Lavash, et al. on Feb. 14, 1995; U.S. Pat. No. 5,558,663 entitled "Absorbent Article Having Undergarment Covering Components With Zones of Extensibility" issued to Weinberger, et al. on Sep. 24, 1996 (which describes an alternative to flaps that are applied by the wearer); and in International Patent Application Serial No. PCT US 96/15957 entitled "Absorbent Article Having Flaps With Step Configuration and Zones of Extensibility" filed on Oct. 3, 1996, in the name of Lash, et al.

The sanitary napkin 20 shown in FIGS. 1-3 may have a deformed region that forms a hinge 70 between the main body portion 22 and at least a portion of the flaps 24. The sanitary napkin 20 preferably also has at least one zone of extensibility (or "zone of differential extensibility") 72 for relieving the stresses on the flaps 24 when they are folded around a panty crotch. These are described in PCT publication WO 97/12576 published on Apr. 10, 1997 titled "Absorbent Article Having Flaps With A Deformed Hinge And Zones Of Extensibility" which is incorporated herein by reference.

The garment surface 20B of the sanitary napkin 20 may include, and preferably does include, fasteners for securing the sanitary napkin in the crotch region of the wearer's undergarment. FIGS. 1 and 2 show the central pad fastener 82 which is adapted to secure the main body portion 22 of the sanitary napkin to the crotch region of an undergarment. The central pad fastener 82 is provided on at least a portion of the garment surface 20B (i.e., the garment facing side of the backsheet) underneath of the absorbent core. In a preferred embodiment, the central pad fastener 82 comprises a pair of spaced apart longitudinally-oriented strips or zones of adhesive that are centered about the longitudinal centerline L.

The garment surface 20B of the flaps 24 may include, and preferably does include, fasteners to assist in maintaining the flaps 24 in position after they are wrapped around the edge of the crotch portion of the panty. The flaps 24 can be maintained in position by attaching the flaps 24 to the undergarment, or to the opposing flap. The flap fastener 84 is provided on the garment surface 20B of the flap 24. In a preferred embodiment, the flap fastener 84 comprises a generally rectangular patch of adhesive on the garment surface 20B of the flap 24.

When the sanitary napkin has first flaps and second flaps as described above, first flaps may have fasteners for securing the sanitary napkin in the crotch region of the wearer's undergarment and the second flaps may have fasteners for securing the sanitary napkin in the back region of the wearer's undergarment.

Any types of fasteners known in the art, such as adhesive fasteners and mechanical fasteners can be used. Fasteners comprising adhesives have been found to work well for this purpose, with pressure-sensitive adhesives being preferred. The adhesive fasteners are more preferably hot melt pressure-sensitive adhesives, which may be selected from the group consisting of styrene rubber based pressure-sensitive hot melt adhesives, styrene butadiene based pressure-sensitive hot melt adhesives, and styrene isoprene based pressure-sensitive hot melt adhesives. However, the fasteners are not limited to adhesive attachment means. For example, the sanitary napkin 20 could be secured to the wearer's undergarment by mechanical fasteners, such as VELCRO, or U.S. Pat. No. 5,392,498 entitled "Non-Abrasive Skin Friendly Mechanical Fastening System" issued to Goulait, et al. on Feb. 28, 1995. Alternatively, the combination of adhesive fasteners and mechanical fasteners may be used. The adhesive fasteners may be covered by removable release liners, central pad release liner and flap release liner. The pressure-sensitive adhesive adhesives should be covered with release liners to keep the adhesives from sticking to extraneous surfaces prior to use.

Skin care compositions are applied to at least a portion of the body contacting surface of the sanitary napkin 20. The skin care composition may be applied to any portion of the body contacting surface of the sanitary napkin 20. If desired, the skin care composition may be applied to a portion of the garment surface of the sanitary napkin 20. However, it is preferable that the skin care composition is not applied adjacent to the adhesive fasteners such as the central pad adhesive fastener 82 and the flap adhesive fastener 84 such that the adhesive of the fastener is not degraded by the skin care composition.

Figure 4:
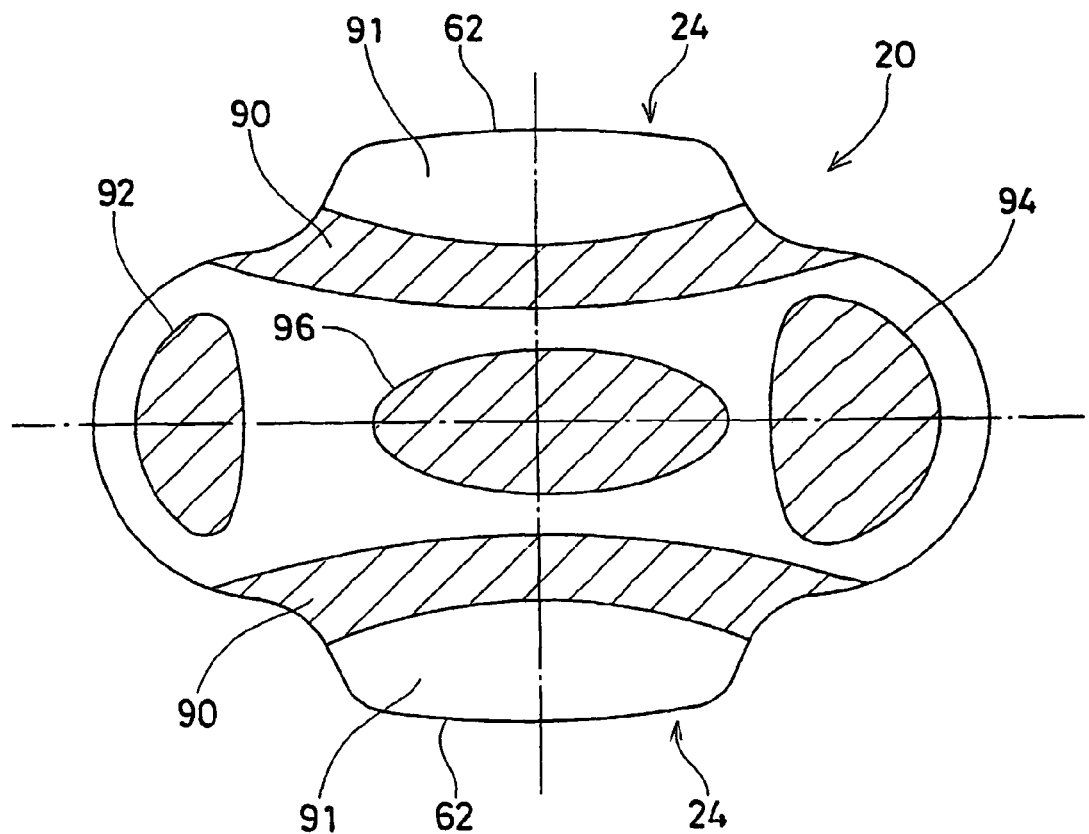
FIG. 4 is a top plan view of the sanitary napkin shown in FIG. 1 with showing areas applied skin care composition.

In the embodiment shown in FIG. 1, the skin care composition is preferably applied to the entirety of the topsheet 38 of the main body portion 22. The skin care composition is also preferably applied to the entire area of the integral topsheet 38 of the flaps 24. Alternatively, the skin care composition may be applied to only a portion of the topsheet 38 of the main body portion 22 and/or a portion of the integral topsheet 38 of the flaps 24. For example, the skin care composition may not be applied to the area of the flaps 24 which is not expected to contact the wearer's skin in a normal use condition of the sanitary napkin 20 (e.g., the distal area 91 of the flap 24 which is adjacent to the distal edge 62 (refer to FIG. 4)). However, if the skin care composition is applied to a portion of the sanitary napkin selectively, it is preferable that the skin care composition is applied to the flap folding area 90 where the flaps 24 are expected to be folded. The skin care composition applied to the flap folding area 90 of the sanitary napkin 20 reduces the wearer's discomfort such as itch and/or abrasion due to rubbing of the flap folding area 90 of the sanitary napkin 20 against the wearer's skin. If the skin care composition is applied to a portion of the sanitary napkin selectively, it is also preferable that the skin care composition is applied to longitudinal end areas 92 and 94 of the sanitary napkin 20. The skin care composition applied to the front end area 92 of the sanitary napkin 20 tends to reduce itch at the front region of the sanitary napkin 20 (which corresponds to the portion of the wearer's body around pubic hairs). The skin care composition applied to the back end area 94 of the sanitary napkin 20 tends to reduce adherence of the sanitary napkin to the wearer's skin at the back region of the sanitary napkin 20 (which corresponds to the portion of the wearer's body around anus). It is also preferable that the skin care composition is applied to central area 96 of the sanitary napkin 20. The skin care composition applied to the central area 96 of the sanitary napkin 20 tends to reduce adherence of the sanitary napkin to the wearer's skin at the central region of the sanitary napkin 20 (which corresponds to the portion of the wearer's body around vulva). In another embodiment, if the sanitary napkin 20 has cuffs along the longitudinal side edges 26, the surface of the cuffs may be treated with the skin care composition.

The barrier sheet is used to reduce, preferably substantially prevent the migration of the skin care composition through the barrier sheet. Therefore, the barrier sheet is useful to protect a desired portion from the skin care composition. The barrier sheet can be used to cover a portion of the sanitary napkin 20, such as the flap adhesive 84, the central pad adhesive 82, a portion of the topsheet 38, or a portion of the backsheet 40 to substantially prevent the migration of the skin care composition thereto. It also may be used to cover a portion of the absorbent core 42 to substantially prevent the migration of the skin care composition thereinto. The barrier sheet may also be used to cover adhesives which join the elements of the sanitary napkin 20, such as the adhesive to join the absorbent core 42 and the topsheet 38, the adhesive to join the absorbent core 42 and the backsheet 40, the adhesive to join the topsheet 38 and the backsheet 40. The barrier sheet may be used for a main wrapper sheet to cover the entirety of the sanitary napkin 20 which is provided with the skin care composition such that the skin care composition does not substantially migrate out through the wrapper.

FIGS. 5-10 show embodiments of the application of the barrier sheet to the sanitary napkin 20. In the embodiments, the sanitary napkin 20 is wrapped by a wrapper 100 comprising several elements. The elements may include: a main wrapper sheet 102 to cover the entirety of the sanitary napkin 20; a central pad adhesive cover 106 disposed on one side of the main wrapper sheet 102 to cover and protect the central pad adhesive 82; and a flap adhesive cover 104 to cover and protect the flap adhesive 84. These elements can comprise integral portions of a single member or article, or they can comprise separate components joined to a member or article. At least one of these elements may comprise a barrier sheet. If the barrier sheet is used for the flap adhesive cover 104 and/or the central pad adhesive cover 106 to cover the flap adhesive 84 and/or the central pad adhesive 82, at least one surface of the barrier sheet is preferably treated releasably.

Figure 5:
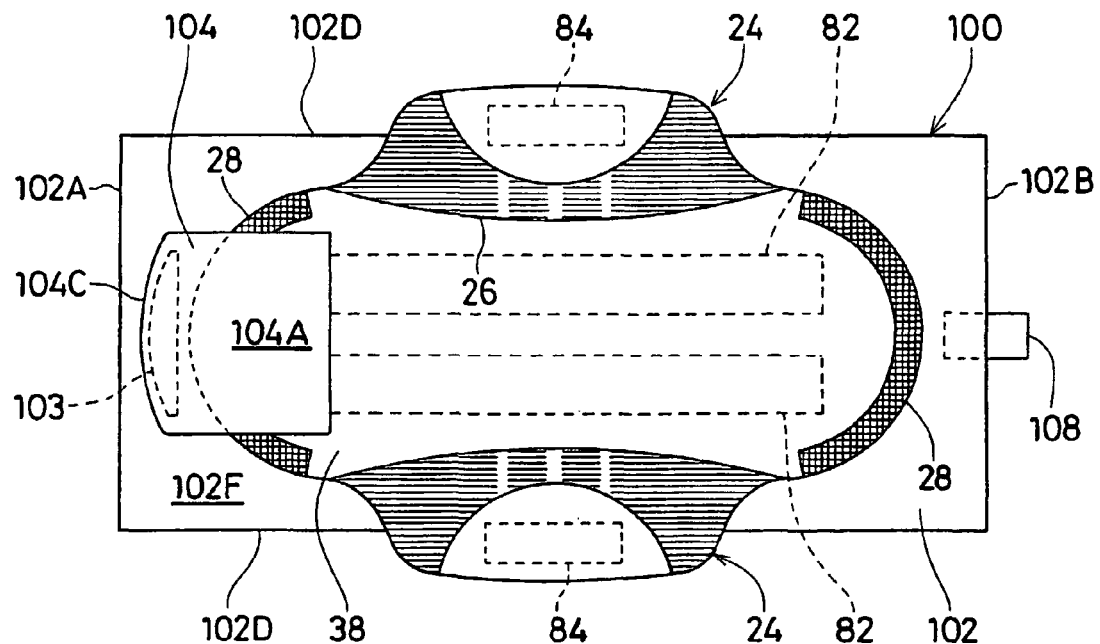
FIG. 5 is a top plan view of one embodiment of a wrapper comprising a barrier sheet in an opened position with the sanitary napkin shown in FIG. 1.
Figure 6:
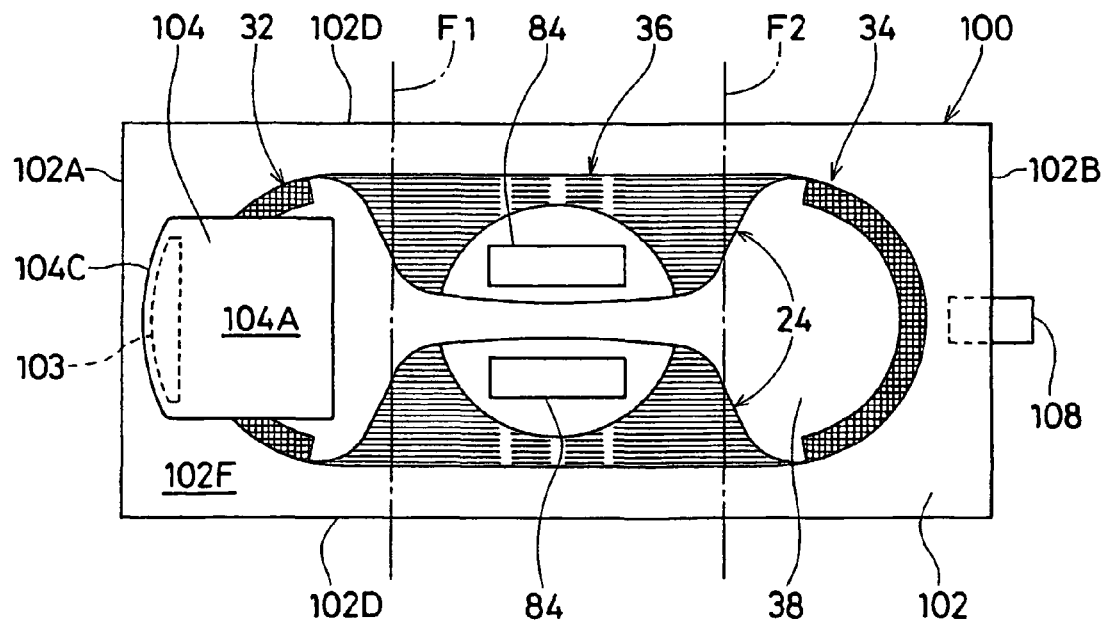
FIG. 6 is a top plan view of the wrapper and the sanitary napkin shown in FIG. 5 with the flaps folded over the topsheet of the sanitary napkin.
Figure 7:
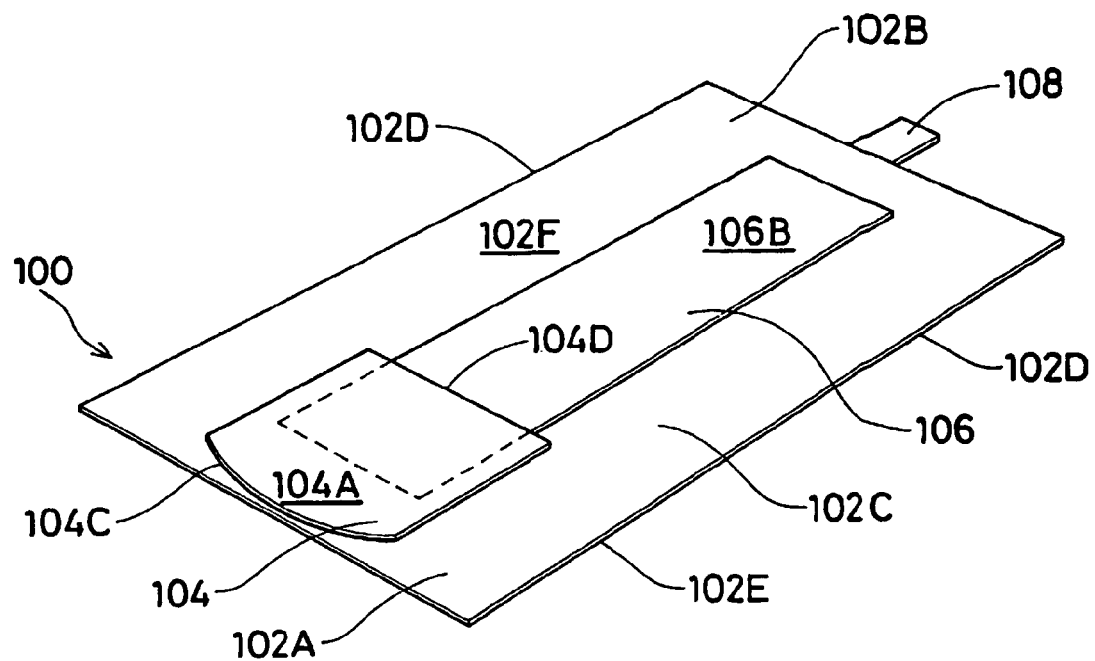
FIG. 7 is a perspective view of the wrapper shown in FIG. 5.
Figure 8:
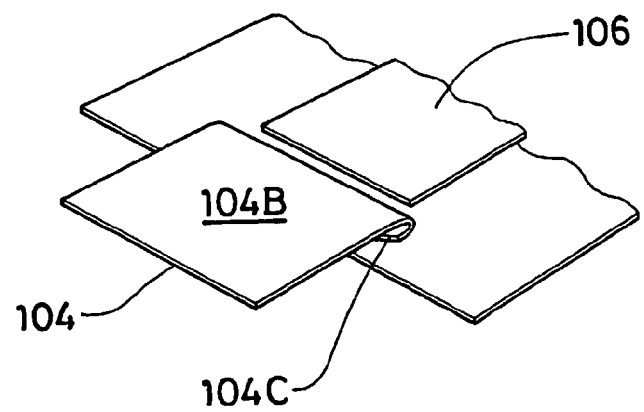
FIG. 8 is a fragmented perspective view of the wrapper shown in FIG. 7 with the free end of the flap fastening cover folded back away from the main wrapper sheet.

The main wrapper sheet 102 may comprise a barrier sheet. The main wrapper sheet 102 comprising the barrier sheet reduces, preferably substantially prevents the migration of the skin care composition applied on the sanitary napkin 20 through the main wrapper sheet 102. The main wrapper sheet 102 (or "wrapper sheet") is the portion of the wrapper 100 which will be folded around the sanitary napkin 20 to provide an individual package for the sanitary napkin 20. As shown in FIGS. 5-7, the main wrapper sheet 102 has two surfaces; an inner surface 102F and an outer surface 102E (the outer surface 102E is not shown in FIGS. 5 and 6). The main wrapper sheet 102 also has longitudinal edge portions 102D, a first end portion 102A and a second end portion 102B. The main wrapper sheet 102 preferably has a size to cover the entirety of the sanitary napkin 20.

The central pad adhesive cover 106 may comprise a barrier sheet. The central pad adhesive cover 106 comprising the barrier sheet reduces, preferably substantially prevents the migration of the skin care composition applied on the sanitary napkin 20 through the central pad adhesive cover 106 toward the central pad adhesive 82. In particular, the adhesives such as the central pad adhesive 82 and the flap adhesive 84 comprises pressure-sensitive hot melt adhesives which could be styrene rubber based pressure sensitive hot melt adhesives, styrene butadiene rubber based pressure-sensitive hot melt adhesives, and styrene isoprene rubber based pressure-sensitive hot melt adhesives. Such adhesives are known to be irresistible with the oil-based composition. When the adhesive is in contact with the oil-based composition, the adhesive chemically degrades via broken balanced mixture of base rubber, tackifier and other components such as plasticizer, and the adhesion of the adhesive becomes weak. Since the barrier sheet reduces, preferably substantially prevents the migration of the skin care composition through the barrier sheet toward the adhesive, the adhesive is substantially protected from the skin care composition and maintains the adhesion.

In the embodiment shown in FIG. 7, the central pad adhesive cover 106 has two surfaces; an inner surface 106B and an opposing surface (the opposing surface is not shown in FIG. 7). The inner surface 106B is releasably treated such that the central pad adhesive cover 106 will release from the central pad adhesive 82 when the wearer moves the sanitary napkin 20 from the wrapper 100. For the release treatment, the inner surface 106B may be provided by attaching a separate release paper or element to the inner surface 106B which is treated with a non-stick material, or by treating all or a portion of the central pad adhesive cover 106 with a non-stick coating, such as by silicone coating a portion of the central pad adhesive cover 106. The opposing surface 106A of the central pad adhesive cover 106 is joined to the inner surface of the main wrapper sheet 102. The central pad adhesive cover 106 also has a pair of longitudinal edge portions and a pair of end portions. The central pad adhesive cover 106 preferably has a size to cover the central pad adhesive 82.

The central pad adhesive cover 106 may be replaced with a release coating directly applied on the inner surface 102F of the main wrapper sheet 102. When the main wrapper sheet 102 comprises a barrier sheet, the central pad adhesive 82 is covered by the main wrapper sheet 102 to be substantially protected from the skin care composition. The release coating may comprise any material known in the art for this purpose, with silicone coatings being preferred. If a coating is used, the coating 106 may be provided by coating only that zone of the main wrapper sheet 102 which will substantially contact the central pad adhesive 82. Alternatively, the entire inner surface 102F of the main wrapper sheet 102 may be coated. Coating the entire inside of a wrapper is disclosed in U.S. Pat. No. 5,181,610 entitled "Flexible Container with Nonstick Interior" which issued to Quick et al. on Jan. 26, 1993.

The flap adhesive cover 104 may comprise a barrier sheet. The flap adhesive cover 104 comprising the barrier sheet reduces, preferably substantially prevents the migration of the skin care composition applied on the sanitary napkin 20 through the flap adhesive cover 104 toward the flap adhesive 84. In the embodiment shown in FIGS. 5 and 6, the flap adhesive cover 104 has two faces; one of which is a non-stick face (or releasable face) 104A, which is capable of releasable attachment with the flap adhesive 84, and an opposite face or side 104B. Preferably, as shown in FIG. 7, the non-stick face 104A of the flap adhesive cover 104 faces away from the main wrapper sheet 102 so that it will be able to releasably adhere to the flap adhesive 84 when the sanitary napkin 20 and the wrapper 100 are in the folded configuration discussed below. The non-stick face 104A is releasably treated such that the flap adhesive cover 106 will release from the flap adhesive 84 when the wearer moves the sanitary napkin 20 from the wrapper 100. For the release treatment, the non-stick face 104A may be treated in the same way as central pad adhesive cover 106.

In the embodiment shown in FIGS. 5-7, the flap adhesive cover 104 also has a pair of longitudinal edge portions, a first end portion (fixed end) 104C, and a second end portion (distal end) 104D. The first end portion 104C of the flap adhesive cover 104 is preferably joined adjacent the first end portion 102A of the main wrapper sheet 102 by an adhesive 103. The second end portion 104D of the flap adhesive cover 104 extends toward the central portion 102C of main wrapper sheet 102 and toward the central portion 36 of sanitary napkin 20 (refer to FIG. 1 as well). Alternatively, the flap adhesive cover 104 may not be joined to a portion of the main wrapper sheet 102. When the wrapper 100 is in the flat configuration shown in FIG. 5, the flap adhesive cover 104 lies over first end region 32 of sanitary napkin 20. The flap adhesive cover 104 can be of any suitable size and shape. Although the figures depict a flap adhesive cover 104 which is only of sufficient width (its dimension measured parallel to the transverse centerline T) to cover and protect the flap adhesives 84. A flap adhesive cover 104, which is of a width equal to the width of the main wrapper sheet 102 or any width therebetween is also contemplated herein.

In the embodiment above, each element of the wrapper 100 (i.e., the main wrapper sheet 102, the central pad adhesive cover 106, the flap adhesive cover 104) may comprise a barrier sheet. Alternatively, only a selected element(s) may comprise a barrier sheet. Preferably, at least the flap adhesive cover 104 comprises a barrier sheet.

The wrapper 100 preferably also comprises an optional package fastener 108 for retaining the package formed by folding the wrapper and sanitary napkin in its folded configuration. The package fastener 108 is preferably both releasably attachable to the package and resealable. The package fastener 108 may be comprised of any releasably attachable and resealable fastener known in the art, such as spots or patches of adhesive, tapes, and mechanical fasteners. A tape tab with a pressure sensitive adhesive located thereon has been found to work well. The package fastener 108 can be disposed at any suitable location on the wrapper 100. In the embodiment shown in FIGS. 5 and 6, the package fastener 108 is preferably positioned at opposing second end portion 102B of the main wrapper sheet 102.

For the initial packaging of the sanitary napkin 20 in the wrapper 100, the garment surface 20B of the main body portion 22 is placed on top of the main wrapper sheet 102. The sanitary napkin 20 is positioned so that the central pad adhesive 82 lies over the central pad adhesive cover 106 on the main wrapper sheet 102. The flaps 24 are then preferably folded over the topsheet 38. Folding the flaps 24 over the topsheet 38 exposes the patches of adhesive 84 disposed on the garment surface of flaps 24 and causes the flaps 24 to cover at least a portion of the topsheet 38. After folding the flaps 24 over the topsheet 38, the sanitary napkin 20 and the main wrapper sheet 102 will then preferably be folded into three sections that are defined by fold axes F1 and F2 shown in FIG. 6. As shown in FIG. 6, the first and second end regions 32 and 34 of sanitary napkin 20 lie longitudinally outboard of the fold axes F1 and F2. The central region 36 of the sanitary napkin 20 lies between preferred fold axes F1 and F2.

Figure 9:
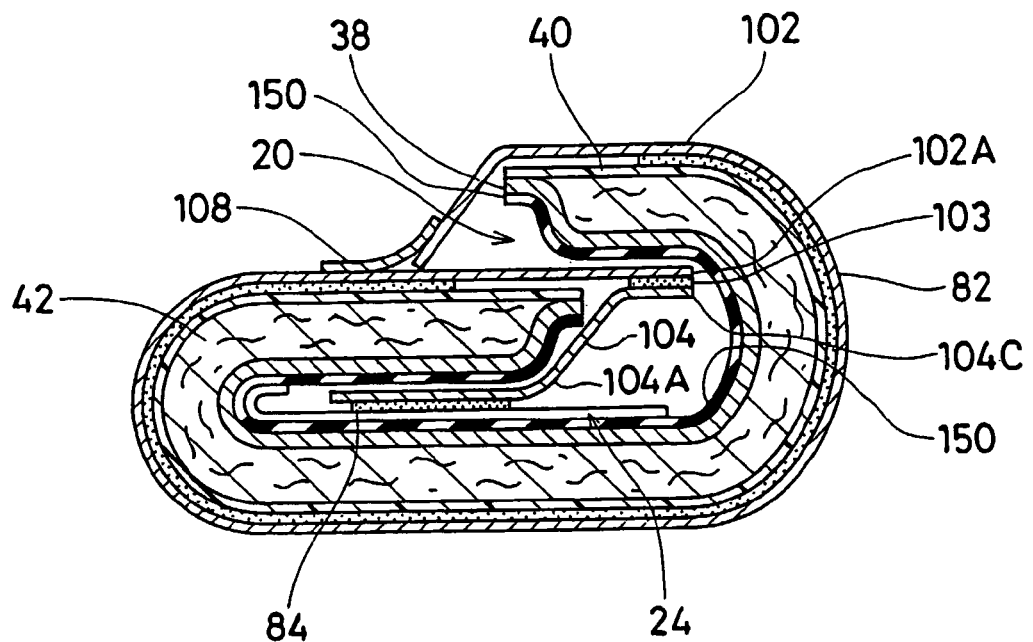
FIG. 9 is a cross-sectional view (taken along the centerline) of the wrapper with the sanitary napkin therein in a folded configuration.

FIG. 9 depicts the package for the sanitary napkin formed by folding the wrapper 100 and sanitary napkin 20 in one preferred configuration for shipment, sale, and convenient carrying by the wearer. As shown in FIG. 9 (refer to FIG. 6 as well), the first end portion 102A of the main wrapper sheet 102, along with the first end region 32 of the sanitary napkin 20, and the flap adhesive cover 104 are folded about first fold axis F1 onto the central region 36 of sanitary napkin 20. When the sanitary napkin 20 and wrapper 100 are folded in this manner, the nonstick face 104A of flap adhesive cover 104 is placed over the flap fasteners 84 and is releasably attached to each adhesive patch 84. In addition, the flap adhesive cover 104 provides a connection between each flap 24 that spans the flaps 24, thereby keeping the flaps 24 in the desired position until flap adhesive cover 104 is removed. The second end portion 102B of the main wrapper sheet 102, along with the second end region 34 of sanitary napkin 20, and the tape tab 108 are then folded about the second fold axis F2. This places these components on top of the first end portion 102A of the main wrapper sheet 102 and the first end region 32 of sanitary napkin 20. By pressing the tape tab 108 onto the exterior of wrapper 100 in the position depicted in FIG. 9, the sanitary napkin 20, its flaps 24 and wrapper 100 remain in the configuration shown.

In the embodiment shown in FIG. 9, the skin care composition layer 150 is applied on all over the surface of the topsheet 38. The flap adhesive 84 is covered by the flap adhesive cover 104 comprising the barrier sheet. In the folded configuration of the sanitary napkin 20 shown in FIG. 9, the flap adhesive cover 104 faces the skin care composition layer 150 and substantially protects the flap adhesive 84 and the adhesive 103 from the skin care composition. The main wrapper sheet 102 may comprise the barrier sheet. The main wrapper sheet 102 substantially protects the adhesive 103 from the skin care composition. The main wrapper sheet 102 also substantially protects a portion of the backsheet 40 from the skin care composition. The main wrapper sheet 102 also protects the central pad adhesive 82 from the skin care composition. The main wrapper sheet 102 also substantially prevents the migration of the skin care composition out through the main wrapper sheet 102. Further, if the central pad adhesive cover is provided, the central pad adhesive cover may comprise the barrier sheet. The central pad adhesive cover substantially protects the central pad adhesive 82 from the skin care composition.

Figure 10:
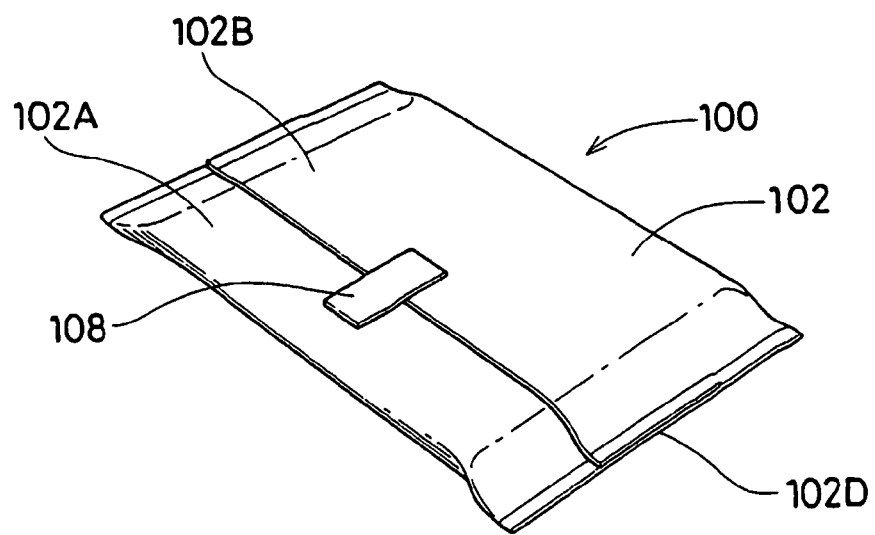
FIG. 10 is a perspective view of the wrapper packaging the sanitary napkin.

Preferably, to complete the individual packaging of the sanitary napkin 20 in the wrapper 100 of the present invention, each longitudinal side edge 102D of the main wrapper sheet 102 is then frangibly sealed after the sanitary napkin 20 and the wrapper 100 are in the folded configuration shown in FIG. 10. The frangible sealing of the side edges 102D of the main wrapper sheet 102 can be accomplished by any suitable sealing technique. By way of example only, the longitudinal side edges 102D may be heat sealed, glued, or ultrasonically bonded. The entire sanitary napkin 20 is thereby protected until the wrapper 100 is opened. Suitable methods for frangibly sealing the longitudinal side edges are described in U.S. Pat. No. 4,556,146 issued to Swanson.

The consumer will ordinarily carry the individually packaged sanitary napkin of the present invention in the form depicted in FIG. 10. The individually packaged sanitary napkin of the present invention depicted in FIG. 10 may be opened by peeling tape tab 108 from the wrapper 100 and breaking the frangible seals along the longitudinal side edges 102D of the main wrapper sheet 102. The consumer can peel the entire wrapper 100 (i.e., the main wrapper sheet 102, the flap adhesive cover 104, and the central pad adhesive cover 106 if provided) from sanitary napkin 20 including the central pad adhesive 82 and the flap adhesives 84 in a single motion. If each element of the wrapper 100 is not connected, the consumer peels each element separately.

Various alternative embodiments of the present invention are possible. For example, instead of being a separate component of the main wrapper sheet, the flap adhesive cover may be an integral portion of the main wrapper sheet. Further, instead of only extending over part of the first end region of the sanitary napkin, the flap adhesive cover could be made longer so that it extends from one of the longitudinal ends of the main wrapper sheet to overlie the central region of the sanitary napkin so that it covers the flap adhesives when the wrapper and sanitary napkin are in an unfolded condition. In this embodiment, the non-stick side of the flap adhesive cover will face inward toward the main wrapper sheet. These and other alternative embodiments are described in PCT publication WO 97/15261 published on May 1, 1997 titled "Absorbent Article Wrapper Comprising Side Flap Fastener Cover" which is incorporated herein by reference.

The sanitary napkin may have first flaps and second flaps. The first flap has fasteners (e.g., adhesive) for securing the sanitary napkin in the crotch region of the wearer's undergarment. The second flap has fasteners (e.g., adhesive) for securing the sanitary napkin in the back region of the wearer's undergarment. A first flap fastener cover and a second flaps fastener cover may be provided to cover the fasteners of the flaps. The first flap fastener cover and the second flap fastener cover may be formed by an integral material. Alternatively, the first flap fastener cover and the second flap fastener cover may be separate materials. If the first flap fastener cover and the second flap fastener cover comprises separate materials, they are preferably joined in the wrapped configuration of the sanitary napkin such that both flap fastener covers are removed in a single motion. More preferably, the first flap fastener cover and the second flap fastener cover are directly or indirectly joined to the main wrapper sheet of the sanitary napkin such that both flap fastener covers and the main wrapper sheet are removed in a single motion. These and other features having first flaps and second flaps are disclosed in, e.g., WO 98/42285 published on Oct. 1, 1998 titled "Absorbent Article Wrapper Comprising A Side Flap Fastener Cover"; WO 98/53781 published on Dec. 3, 1998 titled "Absorbent Article Wrapper Comprising A Side Flap Fastener Cover"; and WO 99/25285 published on May 27, 1999 titled "Absorbent Article Wrapper Comprising A Side Flap Fastener Cover", which are incorporated herein by reference. When the sanitary napkin has first flap fastener cover and second flap fastener cover, both covers may be comprise a barrier sheet.

Figure 11:
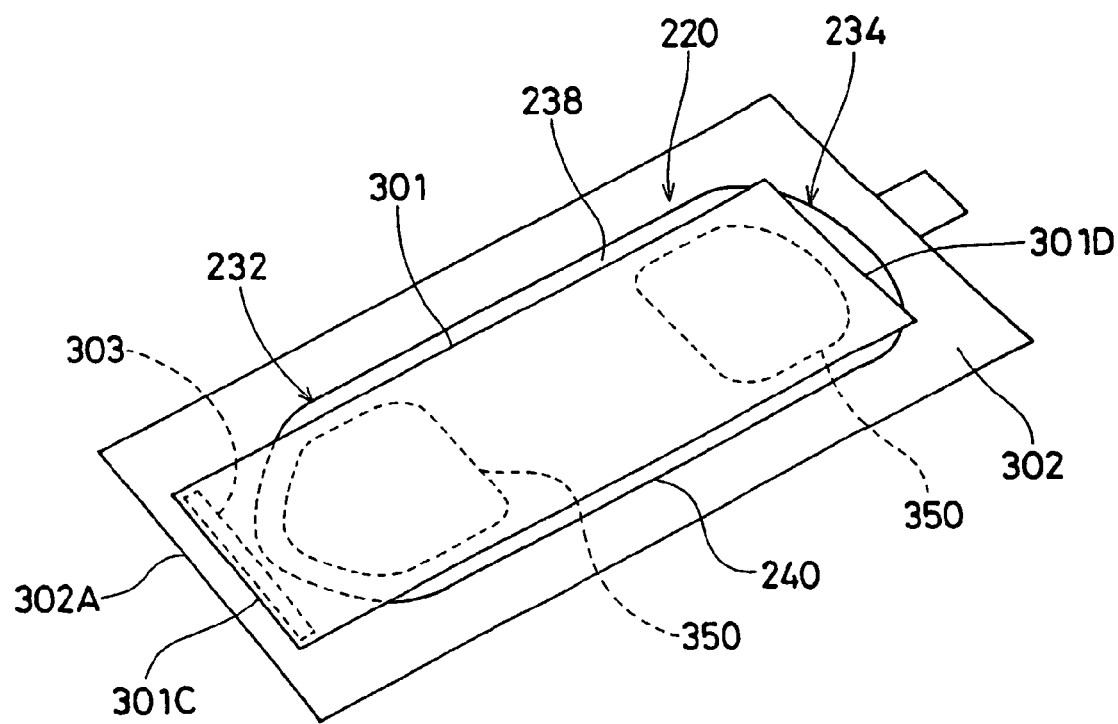
FIG. 11 is a perspective view of an alternative embodiment of a wrapper comprising a barrier sheet in an opened position with an alternative embodiment of a sanitary napkin.

FIG. 11 shows another embodiment of the application of the barrier sheet to the sanitary napkin 220. In the embodiment shown in FIG. 11, the sanitary napkin 220 is placed on the main wrapper sheet 302 such that the topsheet 238 faces upwardly and the backsheet 240 faces the main wrapper sheet 302. The skin care composition is applied on a portion of the first end region 232 of the sanitary napkin 220 and a portion of the second end region 234 of the sanitary napkin 220. Alternatively, the skin care composition may be provided on any portion of the sanitary napkin 220. The topsheet cover 301 is provided to cover the skin care composition layer 350. The topsheet cover 301 comprises a barrier sheet. When the topsheet cover 301 comprises the barrier sheet and covers the skin care composition layer 350, the topsheet cover 301 reduces, preferably substantially prevents the migration of the skin care composition from the topsheet to other portions of the absorbent article, such as a portion of the main wrapper sheet which may come in contact with the topsheet in case the topsheet cover is provided.

The topsheet cover 301 has a pair of longitudinal edge portions, a first end portion 301 C and a second end portion 301D. The first end portion 301D of the topsheet cover 301 may be joined to the first end portion 302A of the main wrapper sheet 302 by, e.g., an adhesive 303. Alternatively, the topsheet cover 301 may be free from attachment to the main wrapper sheet 302. The topsheet cover 301 may have any size as far as the topsheet cover 301 can cover the skin care composition layer which is applied on the topsheet 238. For example, when the skin care composition is applied on the entirety of the topsheet 238, the topsheet cover 301 may have a size which is larger than the size of the topsheet 238.

Numerous other embodiments of the sanitary napkin 20 are possible. For example, the main body portion of the sanitary napkin can be provided in the form of a compound sanitary napkin that has its components bonded as described herein for improved integrity and acquisition. General descriptions of compound sanitary napkins are found in P&G's U.S. Pat. No. 4,425,130 entitled "Compound Sanitary Napkin" issued to DesMarais, et al. on Jan. 10, 1984, and in Statutory Invention Registration H1614 entitled "Body Fitting Compound Sanitary Napkin", published in the name of Mayer, et al. on Nov.

5, 1996. To form the compound sanitary napkin, a sanitary napkin such as that described herein can serve as the panty protector (or "base pad") and a tube of absorbent material wrapped by a topsheet (or "primary menstrual pad") can be placed on top of the sanitary napkin and attached thereto at the ends. The fusion bonding on the base pad is preferably distributed in the same manner as shown on the drawings herein. The attachment of the tube to the sanitary napkin is preferably achieved by fusion bonding extensions of the topsheet material at the ends of the tube to the base pad. In some preferred embodiments of such a compound sanitary napkin, there may also be attachment between the ends of the tube of absorbent material and the base pad. The tube of the compound sanitary napkin can be attached to the base pad between its ends by any suitable attachment means, such as by adhesives.

The skin care composition may be applied to the body contacting surface of other types of absorbent articles. Such absorbent articles having a body contacting surface include, but not limited to, tampons, interlabial absorbent articles, panti-liners, incontinence articles, diapers including infant diapers, training pants, adult incontinence diapers, etc. The barrier sheet may be provided with such absorbent articles having skin care composition to reduce, preferably substantially prevent the migration of the skin care composition through the barrier sheet.

Herein "tampon" refers to any type of absorbent structure which is inserted into the vaginal canal or other body cavities for the absorption of fluid therefrom. The basic tampon structures are described in U.S. Pat. No. 1,926,900 issued to Haas on Sep. 12, 1933; U.S. Pat. No. 1,946,911 issued to Haas on Jul. 3, 1934; and U.S. Pat. No. 3,322,123 issued to Giswold, et al. on May 30, 1967.

Herein "interlabial absorbent article" refers to an absorbent device that is insertable into the interlabial space of a female wearer for catamenial purposes, incontinence barrier, or both. Suitable interlabial absorbent articles are disclosed in, e.g., U.S. Pat. No. 5,762,644 entitled "Toilet-Disposable Absorbent Interlabial Device" issued to Osborn, et al. on Jun. 9, 1998; PCT Publication No. WO 98/29078 entitled "Thin Comfortable Interlabial Absorbent Structure" published in the name of Osborn, et al. on Jul. 9, 1998; U.S. Pat. Des. 404,814 entitled "Interlabial Absorbent Device" issued to Mayer on Jan. 26, 1999; U.S. application Ser. No. 09/071, 425, filed on May 1, 1998 in the name of Brown, et al.

The terms "panty liner" or "panti-liner" refer to absorbent articles that are less bulky than sanitary napkins which are generally worn by women between their menstrual periods. Suitable absorbent articles are disclosed in, e.g., U.S. Pat. No. 4,738,676 entitled "Pantiliner" issued to Osborn on Apr. 19, 1988.

Herein "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in, e.g., U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704, 115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992).

Herein "diaper" refers to an absorbent article generally worn by infants, and incontinent persons that is worn about the lower torso of the wearer. Suitable diapers are disclosed in, e.g., U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; and U.S. Pat. No. 5,554,145 issued to Roe et al. on Sep. 10, 1996.

Herein "training pants" refers to disposable garments having fixed sides and leg openings. Training pants are placed in position on the wearer by inserting the wearer's legs into the leg openings and sliding the training pant into position about the wearer's lower torso. Suitable training pants are disclosed in, e.g., U.S. Pat. No. 5,246,433, issued to Hasse, et al. on Sep. 21, 1993.

The skin care composition may be applied to a portion of or the entirety of the body contacting surface of absorbent articles. For example, the skin care composition may be applied on a portion of or the entirety of the topsheet of the absorbent articles. If the absorbent article has other portions which contact the wearer's skin such as cuffs, the skin care composition may be applied on a portion of or the entirety of those portions. Herein "cuff" includes leg cuffs including barrier cuffs, gasketing cuffs, combinations and variations thereof; transverse barriers and pockets/spacers; side panels; as well as waist cuffs including waist flaps, waistbands, waist-caps, and unitary waistcap/waistbands; and combinations of all or some of these cuffs.

Representative topsheets treated with a skin care composition are described in, e.g., U.S. Pat. No. 5,643,588, "Diaper Having a Lotioned Topsheet", issued to Roe, Bakes & Warner on Jul. 1, 1997; and U.S. Pat. No. 5,635,191, "Diaper Having a Lotioned Topsheet Containing a Polysiloxane Emollient", issued to Roe & Mackey on Jun. 3, 1997; U.S. Pat. No. 5,609,587, "Diaper Having a Lotioned Topsheet Comprising a Liquid Polyol Polyester Emollient and an Immobilizing Agent", issued to Roe on Mar. 11, 1997; and U.S. Pat. No. 5,607,760, "Disposable Absorbent Article Having a Lotioned Topsheet Containing an Emollient and a Polyol Polyester Immobilizing Agent", issued to Roe, on Mar. 4, 1997; each of which are incorporated herein by reference. Methods for delivering a skin care composition via the repeated use of absorbent articles having such treated topsheets are disclosed in U.S. patent application Ser. No. 08/926,532 "A Method For Maintaining or Improving Skin Health", Elder, et al., filed on Sep. 10, 1997; U.S. patent application Ser. No. 08/926,533 "A Method For Improving Skin Condition", Van Rijswijck, et al. filed on Sep. 10, 1997; and U.S. patent application Ser. No. 08/908,852 "Diaper Having A Lotioned Topsheet", Roe, et al. filed on Aug. 8, 1997; each of which is incorporated herein by reference. Representative cuffs treated with a skin care composition are described in, e.g., U.S. patent application Ser. No. 08/766,386 "Absorbent Articles Having Lotioned Leg Cuffs", Schulte et al, filed on Dec. 3, 1996; U.S. patent application Ser. No. 08/840,039 "Absorbent Articles Having Lotioned Leg Cuffs Containing a Polysiloxane Emollient", Schulte et al, filed on Apr. 24, 1997; U.S. patent application Ser. No. 08/962,310 "Absorbent Article Having cuffs and Topsheet with Skin Care Composition Disposed Thereon", Schulte et al, filed on Oct. 31, 1997; U.S. patent application Ser. No. 08/962,312 "Absorbent Article Having cuffs and Topsheet with Skin Care Composition(s) Disposed Thereon", Vanri et al, filed on Oct. 31, 1997; each of which is incorporated herein by reference. Representative interlabial absorbent articles treated with a skin care composition are disclosed in, e.g., U.S. patent application Ser. No. 08/869,897 "Emollient-Treated Absorbent Interlabial Device", Osborn et al, filed on Jun. 5, 1997; U.S. patent application Ser. No. 08/869,700 "Absorbent Interlabial Device Treated With A Polysiloxane Emollient", Osborn et al, filed on Jun. 5, 1997;

each of which is incorporated herein by reference. Representative absorbent articles having breathability treated with a skin care composition are disclosed in, e.g., U.S. patent application Ser. No. 08/926,566 "Disposable Absorbent Articles Providing a Skin Condition Benefit", ELDER et al., filed on Sep. 10, 1997.

B. Skin Care Composition.

The skin care composition(s) preferably delivers skin effects. It is preferred that the skin care composition should provide a protective, nonocclusive function (e.g., a relatively liquid impervious but vapor pervious barrier) to avoid skin hyperhydration and skin exposure to materials contained in body exudates; an abrasion minimizing function to reduce skin irritation in the areas where the body contacting surface of absorbent articles contact the wearer's skin; or contain agents that deliver, either directly or indirectly, skin care benefits. For example, indirect benefits include improved removal of skin irritants such as menses, feces or urine. The composition may be in a variety of forms, including, but not limited to, emulsions, lotions, creams, ointments, salves, powders, suspensions, encapsulations, gels, and the like.

The skin care compositions may be solid or semisolid at 20° C. and are solid or semisolid at 40° C. Herein, "semisolid" means the skin care composition has a viscoelastic property (i.e., when no shear stress is applied, the skin care composition has the appearance of a solid. However, as shear stress is increased, the skin care composition can be made to flow as a fluid.) This property ensures the stability of the skin care composition under static conditions (e.g., under condition where the product is in storage and/or transportation) and maximize the availability of the skin care composition transferred to the skin for the skin effects under mechanical shear (e.g., under condition where the product is worn by the wearer and shear stress is applied to the skin care composition).

The skin care composition may have viscosity of more than about $10^5$ Poise under shear stress of less than about $3 \times 10^4$ dynes/cm$^2$, and viscosity of less than about $10^2$ Poise under shear stress of more than about $10^6$ dynes/cm$^2$, at 40° C. Preferably, the skin care composition may have viscosity of more than about $10^6$ Poise under shear stress of less than about $3 \times 10^4$ dynes/cm$^2$, and viscosity of less than about $10^1$ Poise under shear stress of more than about $10^6$ dynes/cm$^2$, at 40° C. Herein, 40° C. represents the temperature which the skin care composition potentially experiences while the article is in storage or transported or worn in contact with the skin. Shear stress of about $3 \times 10^4$ dynes/cm$^2$ represents the maximum shear stress applied to the skin care composition while the article is in storage or transported. Shear stress of about $10^6$ dynes/cm$^2$ represents the shear stress applied to the skin care composition at least once while the article is worn. Viscosity of about $10^5$ Poise is the lowermost viscosity required for preventing the skin care composition from migrating in storage or transportation. Viscosity of more than about $10^6$ Poise is more preferable to prevent the skin care composition from migrating. Viscosity of about $10^2$ Poise is the uppermost viscosity required for obtaining the effective lubrication between the wearer's skin and the body contacting surface of the article and transfer of the skin care composition onto the wearer's skin. Viscosity of less than about $10^1$ Poise is more preferable for effective lubrication and transfer of the skin care composition. Viscosity at various shear stress should be measured by available Rheometers such as cone to plate or plate to plate type Rheometers (e.g. Rheometer SR-2000, Rheometrics Inc.), at 40° C.

Figure 12:
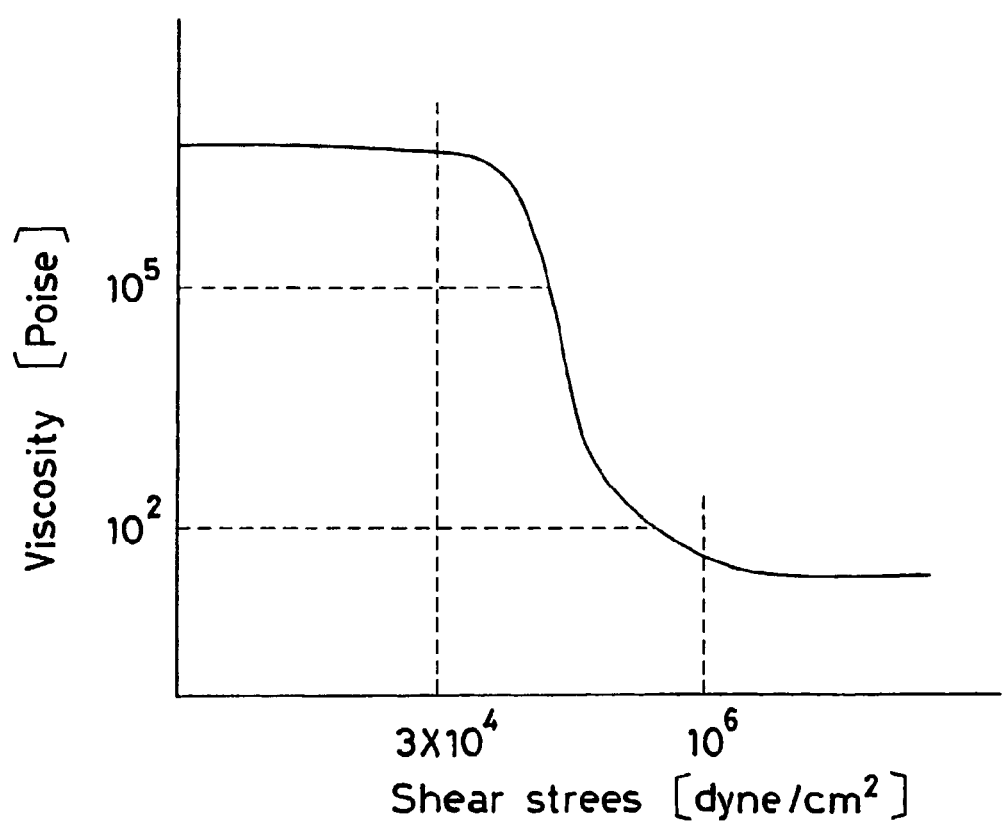
FIG. 12 is a graph of shear stress vs. viscosity of one example of skin care composition.

FIG. 12 shows a graph of shear stress vs. viscosity of one example of preferred skin care composition. When the skin care composition has viscosity of more than about $10^5$ Poise under shear stress of about less than $3 \times 10^4$ dynes/cm$^2$ at 40° C., the skin care composition has less tendency to migrate into the interior of the article in storage or transportation and has more tendency to remain on the body contacting surface of the article. When the skin care composition has viscosity of less than about $10^2$ Poise under shear stress of more than about $10^6$ dynes/cm$^2$ at 40° C., the skin care composition has more tendency to transfer to the wearer's skin. Thus, the skin care composition tends to remain stable on the body contacting surface of the article in storage or transportation, thereby requiring less initial amount of skin care composition disposed on the body contacting surface. Once the absorbent article is worn by the wearer, the skin care composition is exposed to higher shear stress than the shear stress in storage or transportation. Thereby, the skin care composition starts to flow and effective amount of the skin care composition is transferred to the wearer's skin. Herein, the term "effective amount of a skin care composition" refers to an amount of a particular composition which, when applied or migrated to ("disposed on") the body contacting surface, will be effective in delivering desirable skin effects mentioned above.

The skin care compositions also may have consistency of not more than about 300, preferably of not more than about 150, more preferably of not more than about 100, at 40° C. Herein "consistency" means resistance against deformation of skin care composition. When the skin care composition has consistency of not more than about 300 at 40° C., the skin care composition has more tendency to remain on the body contacting surface of the absorbent article. Consistency can be measured by Penetrometer described in ASTM D5, at 40° C. The Penetrometer which is used for measuring consistency is supplied by Petrolab Company, 874 Albany-Shaker Road, Latham, N.Y., under the designation of PNR-10.

The effective amount of composition disposed on the body contacting surface will depend, to a large extent, on the particular skin care composition used, a portion of the body contacting surface where the skin care composition is applied, and/or a product form (e.g., diaper, sanitary napkin, etc.). Nonetheless, the minimum quantity of the skin care composition disposed on at least a portion of the body contacting surface of absorbent articles will preferably be not less than about 0.05 mg/in$^2$ (0.0078 mg/cm$^2$), more preferably not less than about 0.1 mg/in$^2$ (0.016 mg/cm$^2$), still more preferably not less than about 0.5 mg/in$^2$ (0.078 mg/cm$^2$). The maximum quantity of the skin care composition disposed on at least a portion of the body contacting surface will preferably be not more than about 80 mg/in$^2$ (12 mg/cm$^2$), more preferably not more than about 25 mg/in$^2$ (3.9 mg/cm$^2$), still more preferably not more than about 5 mg/in$^2$ (0.8 mg/cm$^2$). These ranges are by way of illustration only and the skilled artisan will recognize that the nature of the composition will dictate the level that must be disposed thereon to achieve the desired skin effects, and that such levels are ascertainable by routine experimentation in light of the present disclosure. Particularly when the skin care composition such as that described in Example 1 is applied to the body contacting surface (i.e., the topsheet 38 of the main body portion 22 and the flap 24) of the sanitary napkin shown in FIG. 1, the quantity of the skin care composition disposed on the body contacting surface preferably ranges from about 0.05 mg/in$^2$ (0.0078 mg/cm$^2$) to about 25 mg/in$^2$ (3.9 mg/cm$^2$), more preferably from about 0.1 mg/in$^2$ (0.016 mg/cm$^2$) to about 10 mg/in$^2$ (1:5 mg/cm$^2$), still more preferably from about 0.5 mg/in$^2$ (0.078 mg/cm$^2$) to about 4 mg/in$^2$ (0.6 mg/cm$^2$).

The skin care compositions may comprise: (1) one or more emollient(s) (2) one or more immobilizing agent(s) to stabilize the emollient(s) (3) one or more skin care active ingredient(s), and (4) other optional components. Although the kind, grade and content of each component of the skin care compositions are arbitrary, the skin care composition including at least one skin care active ingredient preferably satisfies viscosity of more than about $10^5$ Poise under shear stress of less than about $3\times10^4$ dynes/cm$^2$, and viscosity of less than about $10^2$ Poise under shear stress of more than about $10^6$ dynes/cm$^2$, at 40° C. Especially, when the skin care composition comprises emollients and immobilizing agents, the selected ranges of quantity of emollients and immobilizing agents help to achieve the above viscosity range. Namely, the skin care composition comprises from about 40 to about 90% of the emollient. Preferably, the skin care composition comprises from about 50 to about 85%, more preferably from about 60 to about 80%, of the emollient. The skin care composition comprises from about 10 to about 60% of the immobilizing agent. Preferably, the skin care composition comprises from about 15 to about 50%, more preferably from about 20 to about 40%, of the immobilizing agent.

1. Emollient

One key component of the skin care composition is one or more emollient(s). The emollients are selected from materials that soften, smoothen, coat, moisturize, lubricate or cleanses the skin. In general, an emollient simultaneously accomplishes several of these objectives such as smoothing, moisturizing and lubricating the skin. The emollient preferably has a viscoelastic consistency at 20° C. However, this is not essential as long as the skin care composition such as the combination of the emollients and the other components (e.g., immobilizing agents) satisfies the viscosity described above.

The emollients are also substantially free of water. Herein, substantially free of water means that water is not intentionally added to the emollients. Addition of water to the emollients is not needed in preparing or using the skin care compositions. However, minor and or trace quantities of water in the emollient that are contained as the results of ambient humidity can be tolerated without adverse effect. Typically, the emollients may contain about 5% or less water, preferably about 1% or less water, most preferably about 0.5% or less water.

The emollients are preferably hydrophobic such that the sweat, feces, and/or the menses form larger contact angle against the emollient than against the skin and or the topsheet of the article. The hydrophobic emollient reduces wetting of the sweat, feces and/or the menses against the skin and or the topsheet of the article, thereby reducing sticky feeling on the wearer's skin.

The emollients include petroleum-based, fatty acid ester type, alkyl ethoxylate type, fatty acid ester ethoxylates, fatty alcohol type, polysiloxane type, or mixtures of them.

Petroleum-based emollients include petrolatum. Petrolatum is a mixture of aliphatic hydrocarbons having alkyl chain length of 16 or more and possesses inherently a jelly appearance and a jelly hand. Petrolatum is also sometimes categorized as a mixture of mineral oil and microcrystalline wax. Herein, mineral oil refers to a fraction of petrolatum having less viscous mixtures of hydrocarbons having alkyl chain length of from 16 to 24. Herein, microcrystalline wax refers to a fraction of petrolatum having more viscous mixtures of hydrocarbons having alkyl chain length of 25 or more. Petrolatum as the emollient provides the smoothness of the skin because of its jelly hand. Also, petrolatum as the emollient coats the skin or can be absorbed by skin, thereby resulting in moisturizing the skin.

Petrolatum contains heavy aliphatic hydrocarbons and light aliphatic hydrocarbons. The heavy aliphatic hydrocarbons and the light aliphatic hydrocarbons can be defined by alkyl chain length of alkanes in petrolatum including both normal chain and isomers. The light aliphatic hydrocarbons of petrolatum tends to migrate faster than the heavy aliphatic hydrocarbons of petrolatum because molecular weight and diameter of molecules determine the flow property (i.e., viscosity) and diffusion rate of aliphatic hydrocarbons. Therefore, it is preferable that the heavy aliphatic hydrocarbons presents more than the light aliphatic hydrocarbons in petrolatum. The amount of the heavy aliphatic hydrocarbons and the light aliphatic hydrocarbons is comparable by weight ((weight=(the number of the molecules)×(molecular weight of the molecules)). Reduction of the light aliphatic hydrocarbons contributes to reduce migration of petrolatum. However, too much heavy aliphatic hydrocarbons may render the skin care composition too hard to flow. Therefore, the balance between the amount of the heavy aliphatic hydrocarbons and the amount of the light aliphatic hydrocarbons should be made. Petrolatum preferably has the heavy aliphatic hydrocarbons having alkyl chain length of from 33-36 more than the light aliphatic hydrocarbons having alkyl chain length of from 23-26. In this case, the ratio of the heavy aliphatic hydrocarbons to the light aliphatic hydrocarbons is preferably between 2.0:1.0 and 1.0:1.0, more preferably between 1.5:1.0 and 1.0:1.0. More preferably, petrolatum has the heavy aliphatic hydrocarbons having alkyl chain length of from 30-36 more than the light aliphatic hydrocarbons having alkyl chain length of from 20-26. In this case, the ratio of the heavy aliphatic hydrocarbons to the light aliphatic hydrocarbons is preferably between 2.5:1.0 and 1.0:1.0, more preferably between 2.0:1.0 and 1.0:1.0. Yet preferably, petrolatum has the heavy aliphatic hydrocarbons having alkyl chain length of from 27-36 more than the light aliphatic hydrocarbons having alkyl chain length of from 17-26. In this case, the ratio of the heavy aliphatic hydrocarbons to the light aliphatic hydrocarbons is preferably between 3.5:1.0 and 1.5:1.0, more preferably between 3.0:1.0 and 2.0:1.0.

Suitable fatty acid esters include those derived from $C_{12}$-$C_{28}$ fatty acids, preferably $C_{16}$-$C_{24}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid esters can also be derived from esters of longer chain fatty alcohols ($C_{12}$-$C_{28}$, preferably $C_{12}$-$C_{16}$) and shorter chain fatty acids e.g. lactic acid such as lauryl lactate and cetyl lactate. Fatty acid esters as the emollients provide the smoothness of the skin. Also, fatty acid esters as the emollients coat the skin, thereby resulting in moisturizing the skin.

Suitable alkyl ethoxylates include $C_{12}$-$C_{22}$ fatty alcohol ethoxylates having an average degree of ethoxylation of from about 2 to about 30. Preferably, the fatty alcohol ethoxylate is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). These alkyl ethoxylates as the emollients are typically used in combination with petrolatum as the emollient, at a weight ratio of alkyl ethoxylate emollient to petrolatum emollient of from about 1:1 to about 1:5, preferably from about 1:2 to about 1:4.

Suitable fatty alcohols include $C_{12}$-$C_{24}$ fatty alcohols, preferably $C_{16}$-$C_{24}$ fatty alcohols, most preferable $C_{18}$-$C_{24}$ alcohols. Representative examples include cetyl alcohol, stearyl alcohol, behenyl alcohol and mixtures thereof. These fatty alcohols as the emollients are typically used in combination with petrolatum as the emollient, at a weight ratio of fatty alcohol emollient to petrolatum emollient of from about 1:1 to about 1:5, preferably from about 1:1 to about 1:2.

Other suitable types of emollients include polysiloxane compounds which sometimes are called silicone compounds or silicone polymer compounds instead. In general suitable polysiloxane compounds include those having monomeric siloxane units of the following structure:

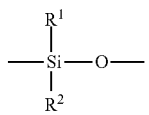

wherein, $R_1$ and $R_2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit. Additionally, the polysiloxane can be either a straight chain, a branched chain or have a cyclic structure. The radicals $R_1$ and $R_2$ can additionally independently be other silaceous functionalities such as, but not limited to siloxanes, polysiloxanes, silanes, and polysilanes. The radicals $R_1$ and $R_2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the article topsheet. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the topsheet of the article by such methods as, for example, emulsifying the polysiloxane in surfactant or providing the polysiloxane in solution with the aid of a solvent, such as hexane, listed for exemplary purposes only. Particular methods for applying polysiloxane emollients onto the topsheet of the article are discussed in more detail hereinafter.

Preferred polysiloxanes compounds are disclosed in U.S. Pat. No. 5,059,282 (Ampulski et al), issued Oct. 22, 1991, which is incorporated herein by reference. Particularly preferred polysiloxane compounds for use as emollients in the skin care compositions include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petrolatum emollient, fatty acid ester emollients, fatty acid ester ethoxylate emollients, alkyl ethoxylate emollients, fatty alcohol emollients, and polysiloxane compound emollients, the emollients can include minor amounts (e.g. up to about 10% of the total emollient) of other, conventional emollients. These other, conventional emollients include propylene glycol, glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$-$C_{28}$ fatty acids; other fatty esters of polyhydroxy alcohols; lanolin and its derivatives. These other emollients should be included in a manner such that the solid or semisolid characteristics of the skin care composition are maintained.

The amount of emollient that can be included in the skin care composition will depend on a variety of factors, including the particular emollient involved, the desirable benefits, the other components in the skin care composition and like factors.

2. Immobilizing Agent

Another key component of skin care compositions is immobilizing agents. Immobilizing agents are capable of thickening emollients of skin care compositions. Immobilizing agents may be soluble in emollients or insoluble in emollients. Without wishing to be bound by the theory, it is believed that immobilizing agents form microscopic networks in the skin care composition (e.g., emollient) to thicken the skin care composition. Herein, "microscopic network" refers to the network whose units are molecules of immobilizing agents being soluble in emollients, or particles of immobilizing agents being insoluble in emollients. Particularly, "microscopic network" of immobilizing agents being soluble in emollients is sometimes referred to as "liquid crystal". In the microscopic network, molecules or particles form flexible/weak connection among molecules or particles.

The immobilizing agent should be homogeneously dispersed in the skin care composition such that less amount of immobilizing agent is required to impart expected thickening. Less amount of immobilizing agent contained in the skin care composition allows more amount of emollient, which is one of the actives for expected skin effects, in the skin care composition. The immobilizing agent homogeneously dispersed in the skin care composition also enables to control variability of the quality of the skin care composition. Preferably, the immobilizing agent has sufficient solubility or dispersability in the emollient. In most cases and preferred cases, the emollients are hydrophobic. In this case the immobilizing agents should be also hydrophobic so that the emollient and the immobilizing agent can achieve a desired homogeneous mixture. The immobilizing agents and the emollients are sometimes compounded while both of them are molten.

The immobilizing agents being soluble in emollients can comprise a component selected from the group consisting of $C_{14}$-$C_{24}$ fatty alcohols, $C_{12}$-$C_{24}$ fatty acids, and $C_{12}$-$C_{24}$ fatty alcohol ethoxylates having an average degree of ethoxylation ranging from 2 to about 30, and mixtures thereof. Preferred immobilizing agents include $C_{16}$-$C_{24}$ fatty alcohols, more preferably $C_{18}$-$C_{24}$ fatty alcohols. Representative examples include stearyl alcohol, arachidyl alcohol, behenyl alcohol, lignoceryl alcohol, and mixtures thereof. Herein, "stearyl alcohol" refers to a mixtured fatty alcohol containing $C_{18}$ fatty alcohol as a major component. Herein, "arachidyl alcohol" refers to a mixtured fatty alcohol containing $C_{20}$ fatty alcohol as a major component. Herein, "behenyl alcohol" refers to a mixtured fatty alcohol containing $C_{22}$ fatty alcohol as a major component. Herein, "lignocaryl alcohol" refers to a mixtured fatty alcohol containing $C_{24}$ fatty alcohol as a major component. Preferably, the immobilizing agent comprises behenyl alcohol. Behenyl alcohol as the immobilizing agent preferably comprises $C_{22}$ fatty alcohol as a major component and a minor quantity of $C_{24}$ fatty alcohol. Behenyl alcohol may also comprise $C_{18}$ fatty alcohol and $C_{20}$ fatty alcohol. By containing a minor quantity of $C_{24}$ fatty alcohol in behenyl alcohol, behenyl alcohol provides the emollients with more stability and more efficiently immobilizes the emollients of the skin care composition. When behenyl alcohol comprises $C_{18}$ fatty alcohol, $C_{20}$ fatty alcohol, $C_{22}$ fatty alcohol, and $C_{24}$ fatty alcohol, the ratio of each component is preferably as follows: from about 50% to about 99.99% of $C_{22}$ fatty alcohol, more preferably from about 63% to about 84.9% of $C_{22}$ fatty alcohol; from about 0.01% to about 3% of $C_{24}$ fatty alcohol, more preferably from about 0.1% to about 2% of $C_{24}$ fatty alcohol; from 0% to about 27% of $C_{20}$ fatty alcohol, more preferably from about 10% to about 20% of $C_{20}$ fatty alcohol; from 0% to about 20% of $C_{18}$ fatty alcohol, more preferably from about 5% to about 15% of $C_{18}$ fatty alcohol. One of preferable behenyl alcohols as the immobilizing agent is Lanette 22 available from Henkel Corp. Cospha, 300 Brookside Avenue, Ambler, Pa. 19002.

Other preferred immobilizing agents include $C_{16}$-$C_{24}$ fatty acids, more preferably $C_{18}$-$C_{24}$ fatty acids selected from the group consisting of stearic acid, behenic acid and mixtures thereof. Behenic acid is most preferred. Still other preferred immobilizing agents include $C_{16}$-$C_{24}$ fatty alcohol ethoxylates having an average degree of ethoxylation ranging from about 5 to about 20. Preferably, the fatty alcohols, fatty acids and fatty alcohols are linear and do not contain branched isomers.

Importantly, these preferred immobilizing agents such as the $C_{18}$-$C_{24}$ fatty alcohols are assumed to provide the microscopic network in the skin care composition, thereby resulting in the skin care composition which is far thicker than only the emollients which are included in the skin care composition. These preferred immobilizing agents such as $C_{18}$-$C_{24}$ fatty alcohols are soluble enough to form homogeneous mixtures of the emollients and the immobilizing agents.

Other types of immobilizing agents being soluble in emollients can be used either alone or in combination with the fatty alcohols, fatty acids, and fatty alcohol ethoxylates described above. Examples of these other types of immobilizing agents includes polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using article topsheets to which the skin care composition is applied, these esters and amides should also be relatively mild and non-irritating to the skin.

Suitable polyhydroxy fatty acid esters will have the formula:

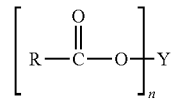

wherein R is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; Y is a polyhydroxy-hydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters comprises certain sorbitan esters, preferably the sorbitan esters of $C_{16}$-$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters comprises certain glyceryl monoesters, preferably glyceryl monoesters of $C_{16}$-$C_{24}$ saturated fatty acids such as glyceryl monostearate, glyceryl monopalmitate, and glyceryl monobehenate. Again, like the sorbitan esters, glyceryl monoester mixtures will typically contain some di- and tri-ester. However, such mixtures should contain predominantly the glyceryl monoester species.

Another class of suitable polyhydroxy fatty acid esters comprises certain sucrose fatty acid esters, preferably the $C_{12}$-$C_{24}$ saturated fatty acid esters of sucrose. Sucrose monoesters and diesters are particularly preferred and include sucrose mono- and di-stearate and sucrose mono- and di-laurate.

Suitable polyhydroxy fatty acid amides will have the formula:

wherein $R^1$ is H, $C_1$-$C_4$ hydrocarbyl, 2-hydroxyethyl, 2-hydroxypropyl, methoxyethyl, methoxypropyl or a mixture thereof, preferably $C_1$-$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)-[$(CHOH)_{n-1}$]-$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl, $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

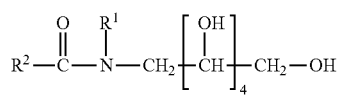

wherein $R^1$ is methyl or methoxypropyl; $R^2$ is a $C_{11}$-$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients being soluble in emollients that can be used as immobilizing agents, either alone, or in combination with the above-mentioned immobilizing agents, include waxes such as carnauba wax, beeswax, candelilla wax, paraffin wax, microcrystalline wax, castol wax, ceresin, esparto, ouricuri, rezowax, polyethylene wax, and other known waxes. Preferably the wax is a microcrystalline wax. An example of a particularly preferred microcrystalline wax is Multiwax W-835, Witco Corporation, One American Lane, Greenwich, CT 06831-2559.

The immobilizing agents being insoluble in emollients are particulate thickeners. Herein "particulate thickener" means the immobilizing agent being in the form of small, finely divided particles. The particulate thickener is able to enhance smooth feeling or lubricant effect of the skin care composition because of its particle structure. For example, fumed silica is so spherical like a "ball" that it can act as a bearing, when shear force is applied, resulting in a lubricant effect. Bentonite or hectorite consists of a plurality of thin layers which can slide easily thus resulting in smooth feeling. The average diameter or the corresponding average diameter may be less than about 100 microns, preferably less than about 20 microns, more preferably less than about 10 microns. When the particle has a different shape from a sphere, the corresponding diameter of the non-spherical particle can be represented by a diameter of a sphere having the same volume as the non-spherical particle. The corresponding diameter can be measured by Laser Particle Analyzer supplied by Honeywell Inc., Honeywell Plaza, Minneapolis, Minn., under the designation of Microtrac X-100.

The particulate thickener is essentially insoluble in the emollient but can be dispersed forming the microscopic network therein and provide a solid structure for the emollient. The particulate thickener can be selected from the group consisting of silica, treated silica, polymethacrylate polymers, polymethacrylate and styrene copolymers, calcium silicate, treated calcium silicate, treated bentonite, treated hectorite, and mixtures thereof. A preferred particulate thickener for use herein is fumed silica. More preferred for use herein is surface-treated fumed silica. Even more preferred is a fumed silica selected from the group consisting of polyalkylsiloxane treated fumed silica, trialkylsilanized fumed silica, dialkyldisilanized fumed silica, and mixtures thereof. Most preferred is a fumed silica selected from the group consisting of polydimethylsiloxane treated fumed silica, trimethylsilanized fumed silica, dimethyldisilanized fumed silica, and mixtures thereof.

Silica is also known as silicon dioxide or silicic anhydride, which can be represented by the chemical formula $SiO2$. A variety of different types of silicas which are useful herein, are known fumed or arced silica, precipitated silica, silica gel, amorphous silica, and silica sols and colloids. Fumed silica, which is also known as arced silica, is produced by the vapor phase hydrolysis of silicon tetrachloride in a hydrogen oxygen flame. Without being limited by theory, it is believed that the combustion process creates silicon dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. Amorphous silicas are generally naturally occurring microcrystalline forms of the material. Silica sols and colloids are dispersions of amorphous silica in an aqueous solution The fumed silica and treated fumed silica preferably have a mean particle size for the agglomerates, i.e., a mean agglomerate particle size, of from about 0.1 microns to about 100 microns, preferably from about 1 micron to about 50 microns, and more preferably from about 10 microns to about 30 microns. The agglomerates are composed of aggregates which having a mean particle size, i.e., a mean aggregate particle size, from about 0.01 microns to about 15 microns, preferably from about 0.05 microns to about 10 microns, more preferably from about 0.1 microns to about 5 microns, and most preferably from about 0.2 microns to about 0.3 microns.

The fumed silica agglomerates typically have active hydroxyl groups. It is desirable to treat these fumed silicas to render the hydroxyl groups less reactive especially when the emollient in the skin care composition is hydrophobic. A useful method of treatment is to coat the fumed silica with a nonpolar organic compound to render the active hydroxyl groups less reactive. Preferred organic compounds for treatment include polyalkylsiloxanes, with polydimethylsiloxanes being most preferred. A commercially available polydimethylsiloxane treated fumed silicas useful herein are sold under the trade name CAB-O-Sil® TS-720 by Cabot Corporation, Tuscola, Ill., or Aerosil R972 by Degussa AG, Germany, both of which have a surface area of around 120 $m^2/g$ and a bulk density of 50 g/L. Another useful method of treatment is to chemically react the hydroxyl groups of the fumed silica with a silanizing agent, e.g., diemthyldichlorosiliane or hexamethyldisilizane. In these chemically treated silicas, the free hydroxyl groups of the silica are replaced with an oxygen-silicon bond of the silanizing agent. A commercially available trimethyl silanized fumed silica is sold under the trade name CAB-O-Sil® TS-530, by Cabot Corporation, Tuscola, Ill., which has a surface area of about 220 $m^2/g$ and a bulk density of 50 g/L. A commercially available dimethyldisilanized fumed silica is sold under the trade name CAB-O-SIL® TS-610, by Cabot Corporation, Tuscola, Ill., which has a surface area of about 120 $m^2/g$ and a bulk density of 50 g/L.

The particulate thickeners also useful herein are polymethacrylate polymers and polymethacrylate and styrene copolymers. These materials are swellable polymers which are useful for absorbing liquid compositions to provide a thickening or gelling effect on the liquid. The polymethacrylate polymers are homopolymers of methacrylic acid esters, preferably the methyl or ethyl esters, which are optionally crosslinked with any of the common crosslinking agents. The polymethacrylate and styrene copolymers are copolymers of methacrylic acid esters, preferably the methyl or ethyl esters, with styrene, which are optionally crosslinked with any of the common crosslinking agents. The crosslinking agent is most typically a material containing two or more unsaturated functional groups. The crosslinking agent is reacted with the monomer units of the polymer or copolymer and is incorporated into the polymer thereby forming links or covalent bonds between two or more individual polymer chains or between two or more sections of the same polymer chain. Non limiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. A particularly useful crosslinked polymethacrylate polymer is sold under the trade name Polytrap® 6603, by Dow Corning Corp., Midland, Mich.

The particulate thickeners also useful herein are treated bentonites and treated hectorites. Bentonite is a colloidal aluminum silicate clay. Hectorite is a clay containing sodium, magnesium, lithium silicon, oxygen, hydrogen, and fluorine. Useful herein especially when the emollient in the skin care composition is hydrophobic are bentonites and hectorites that have been treated with various organic compounds to render the clays less polar. Herein "treated" means that these materials have been coated with the organic compound. Non limiting examples of treated bentones include stearalkonium hectorite; quaternium-18 bentonite; quaternium-18 hectorite; castor oil and stearalkonium hectorite and propylene carbonate; isopropyl myristate and stearalkonium hectorite and propylene carbonate; isododecane and quaternium-18 hectorite and propylene carbonate; lanolin oil and isopropyl palmitate and stearalkonium hectorite and propylene carbonate and propylparaben; propylene glycol dicaprylate/dicaprate and stearalkonium hectorite and propylene carbonate; mineral oil and quaternium-18 hectorite and propylene carbonate; mineral oil and quaternium-18 hectorite and SD alcohol 40; petroleum distillates and quaternium-18 hectorite and propylene carbonate; C12-15 alkyl benzoate and stearalkonium hectorite and propylene carbonate; cyclomethicone and quaternium-18 hectorite and SD alcohol 40; cyclomethicone and quaternium-18 hectorite and propylene carbonate; and mixtures thereof.

The particulate thickeners also useful herein are calcium silicate and treated calcium silicate. Common forms of calcium silicate include CaSiO3, CaSiO4, and CaSiO5. These materials are also known as calcium salts of silicic acid. The calcium silicates can be treated with a wide variety of nonpolar organic compounds to make the materials more hydrophobic. Useful calcium silicates include the following commercially available materials: Hubersorb (Huber Corp., Harve de Grace, Md.), and Micro-Cel C, Micro-Cel E, and Micro-Cel T-38 (Celite Corp., Denver, Colo.)

Most of all the particulate thickeners above can be easily dispersed in the emollient in the skin care composition thanks to the surface treatments. Instead of the surface treatments or in combination of the treatments some emulsifiers are sometimes useful.

The amount of immobilizing agents that can be included in the skin care composition will depend on a variety of factors.

3. Skin Care Active Ingredients

Various skin care active ingredients may be incorporated in the skin care composition. These skin care actives preferably provides skin care benefits. These active ingredients include, but not limited to, skin care agents, proton donating agents, enzyme inhibitors, or mixtures thereof. The skin care composition allows to reduce the initial amount of the skin care active ingredients incorporated because of less migration in storage or transportation while delivering effective amount of skin care active ingredients to the skin in use.

The skin care agents may be added to deliver a therapeutic and/or skin protective benefit. It will be recognized that of the numerous materials useful in the skin care compositions delivered to skin, those that have been deemed safe and effective skin care agent and mixtures thereof are logical materials for use herein. Such materials include Category I actives as defined by the U.S. Food and Drug Administration's (FDA) Tentative Final Monograph on Skin Protectant Drug Products for Over-the-Counter Human Use (21 C.F.R. §347), which presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Food and Drug Administration's Tentative Final Monograph on Skin Protectant Drug Products for Over-the-Counter Human Use (21 C.F.R. §347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, buffered mixture of cation and anion exchange resins, corn starch, trolamine, and the like. Further, other potential materials are Category II actives as defined by the U.S. Food and Drug Administration's Tentative Final Monograph on Skin Protectant Drug Products for Over-the-Counter Human Use (21 C.F.R. §347), which include: bizmuth subnitrate, boric acid, ferric chloride, polyvinyl pyrrolidone-vinyl acetate copolymers, sulfur, tannic acid, and the like. The skin care agent may be selected from these materials and mixtures thereof. As mentioned above, the materials for use should be safe.

The skin care composition may include between about 0.001% and about 50% of the skin care agent. The concentration range of the skin care agents in the skin care composition varies from material to material. Below table shows preferred skin care agents for use and its concentration ranges in the skin care composition.

|  | Possible concentration range (%) | Preferred concentration range (%) |
| --- | --- | --- |
| allantoin | 0.2-5 | 0.5-2 |
| aluminum hydroxide gel | 0.1-10 | 0.15-5 |
| calamine | 0.2-40 | 1-25 |
| cocoa butter | 30-50 | 40-50 |
| dimethicone | 0.2-40 | 1-30 |
| glycerine | 5-50 | 20-45 |
| kaolin | 2-30 | 4-20 |
| petrolatum | 30-50 | 40-50 |
| shark liver oil | 0.1-10 | 1-5 |
| white petrolatum | 30-50 | 40-50 |
| zinc acetate | 0.05-10 | 0.1-2 |
| zinc carbonate | 0.05-10 | 0.2-2 |
| zinc oxide | 0.1-25 | 0.3-8 |

It should be understood that the skin care composition may include the materials listed above beyond its range. For example, when the skin care composition comprises 40% of petrolatum as an emollient and 50% of petrolatum as an skin care agent (another 10% may be immobilizing agent), 90% of the skin care composition may be petrolatum.

Many of the FDA monographed skin care agents are currently utilized in commercially available skin care products, such as A and D® Ointment, Vaseline® Petroleum Jelly, Desitin® Diaper Rash Ointment and Daily Care® ointment, Gold Bond® Medicated Baby Powder, Aquaphor® Healing Ointment, Baby Magic® Baby Lotion, Johnson's Ultra Sensitive® Baby Cream. Those skin case ingredients and/or products may be incorporated to create treated articles.

The proton donating actives may be added to help maintain a wearer's skin at its natural acidic pH. For example such proton donating actives can be effective in neutralizing any high pH (i.e. >7) components of bodily exudates. Chemically suitable proton donating actives are effective in helping maintain skin pH in at least a slightly acidic condition. A non limiting and exemplary listing of proton donating actives includes: monomeric organic acids; acid salts of organic or inorganic acids; and polymeric organic acids and salts thereof. Certain combinations of an acid and a salt thereof, commonly known as buffers, are also suitable as long as an aqueous solution of the acid/salt combination has a pH less than 7. A suitable acid or acid salt should have at least one pKa between about 2.0 and about 6.5. The preferred range of pKa values for suitable proton donating actives is between about 2.5 and about 5.0. Preferred proton donating actives include pharmaceutically acceptable monomeric and polymeric organic acids.

Exemplary monomeric organic acids suitable for use include: citric, malic, adipic, glutaric, lactic, sorbic, salicylic, tartaric, maleic, fumaric, malonic, glycolic, and succinic acids.

Exemplary organic polymeric acids include: acidic vinyl polymers, for example, homopolymers of unsaturated carboxylic acid and anhydride monomers such as acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride, copolymers of unsaturated monomeric acids with suitable co-monomers, and partially neutralized salts of such polymers; acidic cellulose derivatives, such as carboxymethyl cellulose at least partially wherein the cellulose derivatives are at least partially protonated, cellulose phosphate, and oxidized cellulose; and cation exchange resins wherein the cation exchange resin is at least partially protonated.

Exemplary inorganic acid salts include alkali metal monohydrogen phosphates, blends of alkali metal monohydrogen and dihydrogen phosphate salts, alkali metal monohydrogen pyrophosphate salts, and blends of alkali metal monohydrogen and dihydrogen pyrophosphate salts.

Materials which can decompose in the environment adjacent to a wearer's skin into a proton donating active are also suitable for use. For example, esterase enzymes in feces (e.g. fecal lipases) can hydrolyze certain esters to provide a proton donating active. Suitable proton donating actives of this type have the formula:

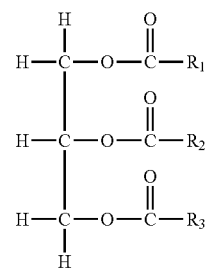

wherein $R_1$, $R_2$ and $R_3$ are independently hydrogen, an alkyl group, an alkenyl group, or a hydroxyalkyl group with from 1 to 4 carbon atoms. An exemplary ester of this type is triacetin.

In order that the proton donating active be effective in helping maintain skin at an acidic pH the proton donating active should be provided at a level of at least 0.01% of the skin care composition; typically at least about 0.5%; preferably at least about 3%. Such suitable proton donating actives may be used as a component of the skin care compositions at a level of between about 0.01% and about 40%, depending on the specific proton donating active chosen. Preferably, the proton donating actives are used at a level of between about 0.5% and about 20% of the skin care composition. In particularly preferred embodiments, the proton donating actives are provided at a level of between about 3% and about 7%.

These and other features of proton donating actives are disclosed in U.S. patent application Ser. No. 09/041,509 entitled "Proton Donating Actives in Absorbent Articles" filed in the name of McOsker, et al. on Mar. 12, 1998, which is incorporated herein by reference.

The inhibitors against enzymes may be added to be available at the skin/urine, skin/feces, skin/menses interfaces to inhibit enzymatic activity on the skin and to reduce or prevent the occurrence of inflammation. Inhibitors of enzyme activity are well known and are typically classified as competitive inhibitors (which compete with the substrate for binding at the active site on the enzyme) and non-competitive inhibitors (which bind to a site other than the active site to inactivate the enzyme). Many enzymes, such as metalloproteases, are inhibited by substances that bind with a metal group on the enzyme. Chelating agents are effective inhibitors of other enzymes that require the presence of metal ions, such as the ions of calcium, cobalt, copper, magnesium, manganese, sodium, potassium, or zinc, for activation. Since enzymes are proteins, antibodies raised against specific enzymes are also effective enzyme inhibitors.

Enzyme inhibitors useful in the absorbent articles described herein will typically have an $IC_{50}$ value of not more than about 500 µM, more typically not more than about 250 µM, and still more typically not more than about 100 µM. As used herein, the term "$IC_{50}$" means the inhibitory concentration (e.g., a micromolar concentration, µM) of a substance (inhibitor) which reduces the rate of substrate cleavage by an enzyme by 50%. The $IC_{50}$ is calculated according to the equation $IC_{50}=[I]/[(v/v_i)-1]$, where [I] is the inhibitor concentration tested, v is the rate of substrate cleavage in the absence of the inhibitor and $v_i$ is the rate of substrate cleavage in the presence of the inhibitor. The $IC_{50}$ of an enzyme inhibitor may be measured by a Purified Enzyme method or by a Fecal Enzyme method which is described in U.S. patent application Ser. No. 09/041,266 entitled "Disposable Absorbent Article Having A Skin Care Composition Containing An Enzyme Inhibitor" filed in the name of Roe, et al. on Mar. 12, 1998. It will be understood that certain enzyme inhibitors (e.g., EDTA) will have higher $IC_{50}$ values but will still be useful in the absorbent articles described herein. For materials for which the molecular weight cannot be determined, such materials will typically reduce enzyme activity by at least 50% at a concentration in the skin care composition of not more than about 5 percent by weight.

Without limitation, any type of enzyme inhibitor may be employed in the skin care compositions transferable to the wearer's skin, including any naturally occurring inhibitor of plant, microbial and/or animal origin (including human) and synthetically manufactured chemical inhibitor. The enzyme inhibitors may be hydrophilic or hydrophobic in nature and may thus be water soluble or soluble in a hydrophobic vehicle. The enzyme inhibitors are preferably present in the skin care composition in a concentration of about 0.001% to about 50% by weight, typically about 0.01% to about 25%, more typically about 0.1% to about 10%, and most typically about 0.1% to about 5%. Because of the variety of enzyme inhibitors employed, the effective concentration of each inhibitor must be separately determined, as known to those skilled in the art.

The enzyme inhibitors may be employed singly or as a mixture of enzyme inhibitors such as a "cocktail" of inhibitors in a single absorbent article. Moreover, different enzyme inhibitors may be employed in skin care compositions in different locations in a single absorbent article.

Because of the wide diversity of enzymes present in body exudates, it is reasonably predictable that materials such as those described below which inhibit certain classes of enzymes (e.g., proteases) may also inhibit enzymes which cleave substrates other than those specified (e.g., proteins and peptides). Hence, inhibitors which inhibit proteases may also inhibit lipases and other esterases, amylases and/or ureases and vice versa.

Inhibitors of enzymes and/or coenzymes most frequently found in body exudates are preferred in the skin care compositions. Thus, the enzyme inhibitors are preferably inhibitors of proteolytic enzymes such as trypsin, chymotrypsin, aminopeptidase and elastase; lipases; bile salts; amylases; and/or ureases.

Exemplary suitable inhibitors of proteases for use that are believed to inhibit the type of protease indicated in parentheses include, but are not limited to, soybean trypsin inhibitor and other plant-derived trypsin inhibitors such as lima bean protease inhibitor, corn protease inhibitor and the like; Bowman-Birk inhibitor (serine, trypsin-like protease inhibitor); pancreatic trypsin inhibitor such as bovine pancreatic basic trypsin inhibitor and other animal-derived pancreatic trypsin inhibitors; egg white trypsin inhibitor (serine, trypsin-like protease inhibitor); ovomucoids containing ovoinhibitors such as from chicken or turkey egg white (trypsin and chymotrypsin inhibitors); chymostatin (serine, chymotrypsin-like protease inhibitor); aprotinin (serine protease inhibitor); leupeptin and its analogs such as propionyl-leupeptin, N-α-t-BOC-deacetylleupeptin (serine and cysteine protease inhibitor); bestatin and its analogs such as epibestatin and nitrobestatin (aminopeptidase metalloprotease inhibitor); amastatin and its analogs such as epiamastatin (aminopeptidase inhibitor); antipain (trypsin inhibitor); antithrombin III (serine protease inhibitor); hirudin (thrombin-like serine protease inhibitor); cystatin (egg white cysteine protease inhibitor); E-64 (trans-epoxysuccinyl-$_L$-leucylamido-(4-guanidino)-butane) and its analogs (cysteine protease inhibitor); $α_2$-macroglobulin (universal endoprotease inhibitor); $α_1$-antitrypsin (trypsin inhibitor); pepstatin and its analogs such as acetyl pepstatin, pepstatin A, Nle-Sta-Ala-Sta (aspartyl protease inhibitor); apstatin (aminopeptidase P inhibitor); (2R)-2-mercaptomethyl-4-methylpentanoyl-b-(2-naphthyl)-Ala-Ala amide (matrix metalloprotease inhibitor); (2R)-2-mercaptomethyl-4-methylpentanoyl-Phe-Ala amide (matrix metalloprotease inhibitor); N-acetyl-Leu-Leu-methioninal (calpain inhibitor);

N-acetyl-Leu-Leu-norleucinal (calpain inhibitor); p-aminobenzyol-Gly-Pro-$_D$-Leu-$_D$-Ala hydroxamic acid (matrix metalloprotease inhibitor); 2(R)-[N-(4-methoxyphenyl-sulfonyl)-N-(3-pyridylmethyl)amino]-3-methylbutano-hydroxamic acid (metalloprotease inhibitor); L-1-chloro-3-[4-tosylamido]-7-amino-2-heptanone-HCl (TLCK), L-1-chloro-3-[4-tosylamido]-4-phenyl-2-butanone (TPCK), tranexamic acid, glycyrrhizic acid, 18-β-glycyrrhetinic acid, colloidal oat extracts, elhibin, zinc salts, iodoacetate, phenylmethylsulfonyl fluoride, phosphoramidon, 4-(2-aminoethyl)-benzenesulfonylfluoride HCl, 3,4-dichloroiso-coumarin, quercetin, and the like, and mixtures thereof.

Chelating agents have also been found to be useful as inhibitors of both proteases and ureases at a concentration of about 0.1% to about 2%. Exemplary chelating agents are phytic acid, nitrilotriacetic acid, EDTA, diethylene triamino pentacetic acid, hyroxyethyl ethylene diamine triacetic acid, and the corresponding acid salts, disclosed in U.S. Pat. No. 5,091,193 issued to Enjolras on Feb. 25, 1992, the disclosure of which is hereby incorporated by reference.

Among preferred protease inhibitors are compounds that exhibit inhibitory activity that is not necessarily restricted to a single class of proteases. Such compounds include, but are not limited to, hexamidine and its salts; pentamidine and its salts; benzamidine, p-aminobenzamidine and their derivatives; and guanidinobenzoic acid and its derivatives such, as those disclosed in U.S. Pat. No. 5,376,655 issued to Imaki et al. on Dec. 27, 1994, the disclosure of which is hereby incorporated by reference. Other preferred protease inhibitors include polymer derivatives of guanidinobenzoic acid disclosed and made in U.S. patent application Ser. No. 09/041,196 entitled "Enzyme Inhibitors" filed in the name of McIver, et al. on Mar. 12, 1998, the disclosure of which is hereby incorporated by reference.

Protease inhibitors that are preferred in the practice are soybean trypsin inhibitor, aprotinin, hexamidine (e.g., hexamidine diisethionate), p-aminobenzamidine, leupeptin, pepstatin A, chymostatin and polymer derivatives of guanidinobenzoic acid (disclosed and made in U.S. patent application Ser. No. 09/041,196 entitled "Enzyme Inhibitors" incorporated by reference above). Particularly preferred protease inhibitors are soybean trypsin inhibitor, hexamidine, p-aminobenzamidine and the foregoing polymer derivatives of guanidinobenzoic acid.

Ureases are known to be inhibited in the presence of trace amounts of heavy metal ions, such as those of silver, copper, and the like. Thus, trace amounts (as little as 0.001% or less) of salts of these metals are useful as urease inhibitors. Other exemplary inhibitors of urease activity include, but are not limited to, acetyl hydroxamic acid and its derivatives, such as cinnamoyl hydroxamic acid and other alkyl hydroxamic acids; phosphoramidate and its derivatives. Such compounds are competitive inhibitors of urease at a concentration of about 2 micromolar (µM). Chelating agents have also been found to be useful as inhibitors of both proteases and ureases at a concentration of about 0.1% to about 2%. Exemplary chelating agents are phytic acid, nitrilotriacetic acid, ethylenediamine tetraacetic acid (EDTA), diethylene triamino pentacetic acid, hyroxyethyl ethylene diamine triacetic acid, and the corresponding acid salts, disclosed in U.S. Pat. No. 5,091,193 incorporated by reference above. Other urease inhibiting compounds are disclosed in U.S. Pat. No. 3,935,862 issued to Kraskin on Feb. 3, 1976, the disclosure of which is hereby incorporated by reference, and include amino acid compounds, such as hydroxyalkylamino acids, sulfhydryl amino acids, aminosulfonic acids, aminophosphonic acid compounds and ether amino acids such as methoxyethyliminodiacetic acid, ethylene-bis-(oxypropylaminodiacetic acid), ethylene-bis-(oxyethyliminodiacetic acid), amino-methyl phosphonic acid (N,N-diacetic acid), and the like, and aminopolycarboxylic acid compounds. including acids and salts diethylenetri-aminepentaacetic acid (DTPA), N-hydroxyethylethylenediaminetriacetic acid (HEDTA), and the like.

Other suitable inhibitors of urease are disclosed in U.S. Pat. No. 5,409,903 issued to Polak et al. on Apr. 25, 1995, the disclosure of which is hereby incorporated by reference. This patent discloses dibasic magnesium phosphate, dialdehyde polysaccharides and zeolite, used alone in combination with each other or with the calcium compounds, calcium acetate, calcium chloride, calcium gluconate and calcium lactate as well as the magnesium compounds, magnesium chloride and magnesium citrate, for inhibition of ureases.

Suitable lipase inhibitors include, but are not limited to, water soluble salts of metals, such as cadmium, cobalt, copper, iron, molybdenum, silver, lanthanum, tin and zinc. Exemplary lipase inhibiting compounds are disclosed in U.S. Pat. No. 4,556,560, hereby incorporated by reference, and include zinc chloride, zinc acetate, zinc nitrate trihydrate, zinc nitrate hexahydrate, zinc sulfate, zinc sulfate heptahydrate, zinc sulfate hexahydrate, iron(II) chloride, iron(II) chloride tetrahydrate, iron(III) chloride, iron(III) chloride monohydrate, iron(III) chloride hexahydrate, iron(II) lactate, iron(III) lactate, iron(III) malate, iron(II) nitrate, iron(III) nitrate hexahydrate, iron(III) nitrate $9H_2O$, iron(II) sulfate and its hydrates, iron(III) sulfate and its hydrates, copper sulfate pentahydrate, tin chloride, cobalt chloride and lanthanum chloride, zinc salts of both saturated and unsaturated monocarboxylic acids having about 6 to about 12 carbon atoms, block copolymers of propylene oxide and ethylene oxide (e.g., marketed as Pluronic® and Tetronic® by BASF Corp.), glycerol triesters of fatty acids having from about 2 to about 20 carbons such as triacetin, and the like. Other useful lipase inhibitors are disclosed in U.S. Pat. No. 5,091,193, hereby incorporated by reference, and include esters of fatty alcohols, such as saturated or unsaturated, linear or branched alkyl acetate, lactate or propionate containing 10 to 20 carbon atoms; saturated or unsaturated, linear or branched zinc salts of fatty acids of 2 to 22 carbon atoms, such as those formed with propionic acid isobutyric acid, caproic acid, undecylenic acid, and the like; zinc salts of aminated acylated acids, such as propionylcysteine, propionyl-hydroxyproline or caproylcysteine, and the like. Lipase inhibitors, such as the foregoing, have been found to be useful at a concentration of about 0.01% to about 10%.

Still other useful lipase inhibitors, disclosed in European Patent Application Serial No. 97120699.0 entitled "Skin Rash Prevention Composition" filed in the name of Palumbo, et al. on Nov. 26, 1997, the disclosure of which is hereby incorporated by reference, include specific ester compounds that act as a substitute substrate for fecal lipases and thereby are competitive lipase inhibitors. These esters have the formulas:

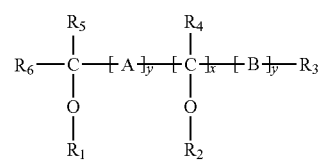

(I)

or

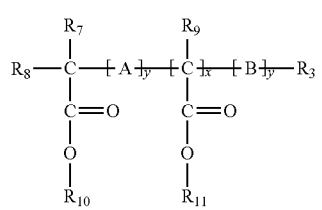

(II)

wherein $R_1$ and each $R_2$ independently are an acyl group with from 2 to 22 carbon atoms, or an alkyl, alkenyl, arylalkyl, hydroxyalkyl group with from 1 to 24 carbon atoms or hydrogen, whereby at least one of $R_1$ and $R_2$ is such an acyl group, $R_3$, $R_4$, $R_5$, $R_6$, $R_7$, $R_8$, and $R_9$ are independently an alkyl, alkenyl, arylalkyl, hydroxyalkyl, alkoxy groups of from 1 to 24 carbon atoms, hydroxy group or hydrogen; $R_{10}$ and $R_{11}$ are independently an alkyl, alkenyl, arylalkyl, hydroxyalkyl, alkoxy groups of from 2 to 24 carbon atoms, hydroxy group or hydrogen; A and B are independently a $C_1$-$C_6$ linear or branched alkylene, alkenylene, alkoxylene, hydroxyalkylene groups; the values of x are independently from 0 to 15; the values of y are independently 0 or 1, with the proviso that when x=2 and y=0, at least one $R_2$ is an alkyl, alkenyl, arylalkyl, hydroxyalkyl group with from 1 to 24 carbon atoms or hydrogen.

Still further examples of lipase inhibitors are those disclosed in U.S. Pat. No. 5,643,874, hereby incorporated by reference, which include: (2S,3S,5S)-5-[(S)-2-formamido-4-methyl-valeryloxy]-2-hexyl-3-hydroxy-hexadecanoic 1,3 acid lactone, also known as tetrahydrolipstatin; (2S,3S,5S,7Z,10Z)-5-[(S)-2-formamido-4-methyl-valeryloxy]-2-hexyl-3-hydroxy-7,10-hexadecadienoic 1,3 acid lactone, also known as lipstatin; 1-(trans-4-isobutylcyclohexyl)-2-(phenylsulfonyloxy)ethanone, also known as FL-386; 4-methylpiperidine-1-carboxylic acid 4-phenoxyphenyl ester, also known as WAY-121898; N-[3-chloro-4-(trifluoromethyl)phenyl]N'-[3-(trifluoromethyl)-phenyl]urea, also known as BAY-N-3176; N-formyl-L-valine-(S)-1-[[(2S,3S)-3-hexyl-4-oxo-2-oxetanyl]methyl]hexyl ester, also known as valilactone; (2S,3S,5S,7Z,10Z)-5-[(S)-2-acetamido-3-carbamoylpropionyloxy]-2-hexyl-3-hydroxy-7,10-hexadecadienoic lactone, also known as esterastin; (3S,4S)-4-[(1S,5R,7S,8R,9R,E)-8-hydroxy 1,3,5,7,9-pentamethyl-6-oxo-3-undecenyl]-3-methyl-2-oxetanone, also known as ebelactone A; (3S,4S)-3-ethyl-4-[(1S,5R,7S,8R,9R,E)-8-hydroxy-1,3,5,7,9-pentamethyl-6-oxo-3-undecenyl]-2-oxetanone, also known as ebelactone B; and 1,6-di(O-(carbamoyl)cyclohexanone oxime)hexane, also known as RHC 80267.

Exemplary inhibitors of bile salts that are coenzymes for lipolytic enzymes and are useful as lipase enzyme inhibitors in the absorbent articles include, but are not limited to, cationic compounds disclosed in European Patent Application Serial No. 97120700.6 entitled "Skin Care Composition" filed in the name of Palumbo, et al. on Nov. 26, 1997, the disclosure of which is hereby incorporated by reference. Such compounds have the formulas:

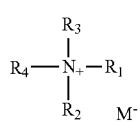

(I)

or

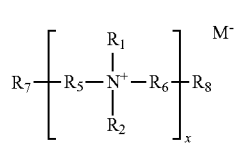

(II)

or an amphoteric compound and preferably an acidity source, the amphoteric compound having at its iso-electric point the formula:

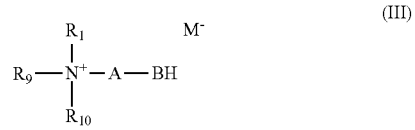

(III)

for preparation of a composition for treatment, prevention or reduction of lipolytic dermatitis of the external skin, wherein $R_1$, $R_2$, $R_3$ and $R_4$ are independently a $C_1$-$C_{22}$ alkyl, alkenyl, aryl, arylalkyl, amidoalkyl, (poly) alkoxy, hydroxyalkyl, or acyl groups, or two or more groups of $R_1$, $R_2$, $R_3$ and $R_4$ form together one or more ring structures; $R_5$, $R_6$ and A are independently a $C_1$-$C_{22}$ alkylene, alkenylene, (poly) alkoxylene, hydroxyalkylene, arylalkylene or amido alkylene groups; $R_7$ and $R_8$ are independently a $C_1$-$C_4$ alkyl, alkenyl, alkoxy group or a hydroxy group or hydrogen; $R_9$ and $R_{10}$ are independently a $C_1$-$C_{22}$ alkyl, alkenyl, aryl, arylalkyl, amidoalkyl, (poly) alkoxy, hydroxyalkyl, or acyl groups, or two or more of the groups $R_1$, $R_9$ and $R_{10}$ form together one or more ring structures; BH is a proton donating group; x is from 2 to 4; and $M^-$ is a counter ion.

Another exemplary suitable bile salt inhibitor is cholestyramine, described in a publication by C. Michael White et al., entitled "Cholestyramine Ointment to Treat Buttocks Rash and Anal Excoriation in an Infant", The Annals of Pharmacotherapy 30: 954-956, September 1996.

Derivatives of p-guanidinobenzoic acid, especially esters of p-guanidinobenzoic acid, have been described as inhibitors of esterases. Such inhibitors are useful in the skin care compositions of the absorbent articles, and are disclosed in U.S. Pat. No. 5,376,655 issued to Imaki et al. on Dec. 27, 1994, the disclosure of which is hereby incorporated by reference.

Suitable amylase inhibitors and/or glucosidase amylase inhibitors include those disclosed in U.S. Pat. No. 5,643,874, hereby incorporated by reference, and include O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4)O-α-D-glucopyranosyl-(1→4)-D-glucose, also known as acarbose; 2(S),3(R),4(S),5(S)-tetrahydroxy-N-[2-hydroxy-1-(hydroxymethyl)-ethyl]-5-(hydroxymethyl)-1(S)-cyclohexamine, also known as voglibose; 1,5-dideoxy-1,5-[(2-hydroxyethyl)imino]-D-glucitol, also known as miglitol; 1,5-dideoxy-1,5-[2-(4-ethoxycarbonylphenoxy)-ethylimino]-D-glucitol, also known as emiglitate; 2,6-dideoxy-2,6-imino-7-(β-D-glucopyranosyl)-D-glycero-L-guloheptitol, also known as MDL-25637; 1,5-dideoxy-1,5-(6-deoxy-1-O-methyl-α-D-glucopyranos-6-ylimino)-D-glucitol, also known as camiglibose; 1,5,9,11,14-pentahydroxy-3-methyl-8,13-dioxo-5,6,8,13-tetrahydrobenzo[a]-naphthacene-2-carboxylic acid, also known pradimicin Q; also known as adiposine; and 1,2-dideoxy-2-[2(S),3(S),4(R)-trihydroxy-5-(hydroxymethyl)-5-cyclohexen-1(S)-ylamino]-glucopyranose, also known as salbostatin. Other suitable amylase inhibitors include tendamistat, trestatins, and those derived from plants, especially from wheat, rice, maize, barley and other cereal grains, beans, and seaweed.

These and other features of enzyme inhibitors are disclosed in U.S. patent application Ser. No. 09/041,232 entitled "Protease Inhibitors in Absorbent Articles" filed in the name of Rourke, et al. on Mar. 12, 1998, and U.S. patent application Ser. No. 09/041,266 entitled "Disposable Absorbent Article Having A Skin Care Composition Containing An Enzyme Inhibitor" filed in the name of Roe, et al. on Mar. 12, 1998, both of which are incorporated herein by reference.

The skin care active ingredients are soluble or insoluble. Insoluble skin care active ingredients may be dispersed in skin care composition with dispersing agents to form homogeneous mixture of skin care composition. It is preferable that the insoluble skin care active ingredients are pre-dispersed in pre-dispersion solvents with dispersing agents. Pre-dispersion solvents may be petroleum-based, fatty acid ester, alkyl ethoxylate, fatty acid ester ethoxylates, fatty alcohol, polysiloxane, or mixtures of them. Further, pre-dispersion solvents may be soluble skin care active ingredients. Exemplary preferable dispersing agents are diethanolamine polyoxyethylene oleyl ether phosphate, polyhydroxystearic acid, polyglyceryl-6 polyricinoleate, neopentyl glycol diisostearate, propylene glycol dicaprate, or mixtures thereof. Other possible dispersing agents are isoelcosane and polyisobutene and quaternium 18, phenyltrimethicone and quaternium-18 hectorite and triethyl citrate, isohexadecane and quaternium-18 hectorite and propylene carbonate, octyldodecanol and quaternium-18 hectorite and propylene carbonate, mineral oil and quaternium-18 hectorite and propylene carbonate, isopropyl myristate and stearalkonium hectorite and propylene carbonate, cyclomethicone and quaternium-18 and SDA 40, lanolin oil and isopropyl palmitate and stearalkonium hectorite and propylene carbonate and propyl paraben, 1-eicosanol, or mixtures thereof.

4. Other Optional Component

Skin care compositions may comprise other optional components. These optional components include water, hydrophilic surfactants, viscosity modifiers, perfumes, film formers, deodorants, opacifiers, solvents, and the like. Stabilizers may be added to enhance the shelf life of the skin care composition such as cellulose derivatives, proteins and lecithin. Hydrophilic surfactants may be added to promote rapid transfer of the fluid (e.g., urine, menses etc.) from the topsheet to the absorbent inner layers of the article. The detail of such hydrophilic surfactant is disclosed in, e.g., U.S. Pat. No. 5,643,588, "Diaper Having a Lotioned Topsheet", issued to Roe, Bakes & Warner on Jul. 1, 1997, which is incorporated herein by reference.

C. Treating Body Contacting Surface with Skin Care Composition

In preparing products treated with skin care compositions, the skin care composition is applied onto at least a portion of the body facing surface of absorbent articles. Any of a variety of application methods that evenly distribute viscous materials can be used. Suitable methods include printing, spraying, coating, brushing, extrusion, or combinations of these application techniques.

The minimum level of skin care composition to be applied onto the body contacting surface of the article is an amount effective for providing the skin effects to the wearer. The level of skin care compositions applied will depend on various factors, including the relative amount of surface area of the body contacting surface not treated with skin care composition, expected skin effects of the skin care composition and the like. The amount of the skin care composition can also vary over the body contacting surface. For example, some portions of the body contacting surface can have greater or lesser amounts of skin care composition than the other portions of the body contacting surface, including portions of the surface that do not have any skin care composition on it.

The skin care composition can be applied onto the entire surface of the body contacting surface or selectively onto the portions of the body contacting surface. For example, if the skin care composition is applied to the topsheet of absorbent article, the way of applying the skin care composition onto the topsheet of absorbent articles is preferable such that the skin care composition is distributed primarily on body facing part of the topsheet. However, if the skin care composition is relatively hydrophobic, it is preferable that the skin care composition is not distributed in the fluid path (such as apertures of the topsheet) and does not block the fluid path to ensure the ability of the topsheet to transmit fluid to the underlying absorbent core. Examples of the pattern of the coating include stripes, dots, circles or the like.

The skin care composition can be applied to the body contacting surface at any point during assembly. For example, the skin care composition can be applied to the body contacting surface of the finished absorbent article before it has been packaged. The skin care composition can also be applied to the body contacting surface before it is combined with the other raw materials to form the finished absorbent article.

The skin care composition is typically applied from a melt thereof to the article. Since the skin care composition melts at significantly above ambient temperatures, it is usually applied as a heated coating to the body contacting surface of the article. The temperature is determined considering primarily the melting point of the skin care composition and the other factors such as lowering of the temperature in the manufacturing process of the article. And the skin care composition is often heated to a temperature in the range from 50° C. to 100° C., more often from 60° C. to 90° C., prior to being applied to the article. Once the melted skin care composition has been applied to the article, it is allowed to cool and solidify to form solidified coating or film on the surface of the body contacting surface. Preferably, the application process is designed to aid in the cooling/set up of the skin care composition. Examples of applying the skin care composition to the body contacting surface is described in, e.g., U.S. Pat. No. 5,643,588, "Diaper Having a Lotioned Topsheet", issued to Roe, Bakes & Warner on Jul. 1, 1997, which is incorporated herein by reference.

D. Barrier Sheet

The barrier sheet is preferably treated to reduce the migration of the skin care composition therethrough. The barrier sheet may comprise a base sheet. The base sheet may be any material, such as a paper or a film. The base sheet may be treated with a composition comprising a component selected from the group consisting of fluorochemicals, hydrophilic polymers, inorganic particles, or mixtures thereof.

Fluorochemicals may be selected from the group consisting of polytetrafluoroethylene, polyfluorinated ethylene propylene, perfluoroalkyl acrylate, polyperfluoroalkoxy, polyhexafluoropropylene, polyhexafluoroisobutylene, polychlorotrifluoroethylene, polyvinylidene fluoride, polyvinyl fluoride, fluoroalkyl salt, copolymers of ethylene, copolymers of propylene, or mixtures thereof. Fluorochemical may be applied to the base sheet of the barrier sheet; in the form of solution or dispersion in water, organic solvent(s) such as alcohol, or mixture of them; or in the form of molten resin. If fluorochemical is applied to the base sheet in the form of solution or dispersion, it may be applied by, e.g., (a) immersing the base sheet in the solution or dispersion then drying, (b) spraying the solution or dispersion onto the base sheet then drying, or (c) coating the base sheet by printing or painting with a brush or a roller then drying. If fluorochemical is applied to the base sheet in the form of molten resin, it may be applied by extrusion laminating. A preferable fluorochemical is fluoroalkyl salt and the most preferable fluorochemical is fluoroalkyl ammonium salt solved in water. This is available under the trade name of Scotchban FC-807A by 3M, Haven 1005, Canadastraat 11, B-2070, Zwijndrecht, Belgium.

Hydrophilic polymers may be selected from the group consisting of polyvinyl alcohol, polyethylene vinyl alcohol, polyvinyl acetate, polyethylene vinyl acetate, polyacrylate, polyethylene acrylate, polymethacrylate, polyethylene methacrylate, polyesters, polyethers, polyimide, polyamide; or mixtures thereof. Hydrophilic polymer may be applied to the base sheet of the barrier sheet in the form of solution or dispersion in water, organic solvent(s) such as alcohol, or mixture of them. If hydrophilic polymer is applied to the base sheet in the form of solution or dispersion, it may be applied by, e.g., (a) immersing the base sheet in the solution or dispersion then drying, (b) spraying the solution or dispersion onto the base sheet then drying, or (c) coating the base sheet by printing or painting with a brush or a roller then drying. If hydrophilic polymer is applied to the base sheet in the form of molten resin, it may be applied by extrusion laminating. A preferable hydrophilic polymer is polyethylene vinyl acetate. This is available under the trade name of ELVAX by DuPont, 1007 Market Street Wilmington, Del. 19898.

Inorganic particles may be selected from the group consisting of kaolin clay, bentonite clay, montmorillonite clay, hectorite clay, tarc, silica, fumed silica, or mixtures thereof. They may be applied to the base paper with some binders. The binder may be selected from the group consisting of polyvinyl alcohol, polyethylene vinyl alcohol, polyvinyl acetate, polyethylene vinyl acetate, polyacrylate, polyethylene acrylate, starch, tragacanth gum, guar gum, arabic gum, karaya gum, dextrin, natural resin, thermoplastic rubber (such as isoprene rubber, butadiene rubber, neoprene rubber, styrene rubber, styrene isoprene rubber, styrene butadiene rubber) based adhesives, or mixtures thereof.

If the binder is a thermoplastic rubber based adhesive, the inorganic particles may be applied to the base sheet by, e.g., super calendaring. If the binder is water soluble, the inorganic particles may be applied to the base sheet by, e.g., printing or painting slurry composed of the inorganic particle, the binder, and small amount (up to 20%) of water onto the base sheet with a brush or a roller.

A preferable component among the inorganic particles above is kaolin clay, bentonite clay, montmorillonite clay, hectorite clay, or mixtures thereof. The most preferable component is kaolin clay, bentonite clay, montmorillonite clay, hectorite clay, or mixtures thereof, with thermoplastic rubber based adhesive as the binder.

The barrier sheet may be treated releasably. Preferably, at least one surface of the barrier sheet is treated releasably when the barrier sheet is used to cover adhesives. For this purpose, the barrier sheet may be treated with a composition comprising a component selected from the group consisting of silicone, a wide variety of fluoropolymers, or mixtures thereof.

Specific Illustrations of Absorbent Article According to the Present Invention

The following examples further describe and demonstrate the preferred embodiments within the scope of the present invention. The examples are given solely for the purpose of illustration, and are not to be construed as limitations of the present invention since many variants thereof are possible without departing from its spirit and scope.

Example 1

A. Preparation of Skin Care Compositions

An oil-based skin care composition (Skin Care Composition A) is made by mixing the following melted components together: Petrolatum made by Witco Corp. under the name Super White Protopet®, and Behenyl Alcohol made by Henkel Corp. under the name Lanette 22. Super White Protopet® is petrolatum. The ratio of the heavy aliphatic hydrocarbons having alkyl chain length of from 27 to 36 to the light hydrocarbons having alkyl chain length of from 17 to 26 is 2.3:1.0. The ratio of the heavy aliphatic hydrocarbons having alkyl chain length of from 30 to 36 to the light aliphatic hydrocarbons aliphatic having alkyl chain length of from 20 to 26 is 1.7:1.0. The ratio of the heavy aliphatic hydrocarbons having alkyl chain length of from 33 to 36 to the light aliphatic hydrocarbons aliphatic having alkyl chain length of from 23 to 26 is 1.3:1.0. Lanette 22 is a mixed linear $C_{18}$-$C_{24}$ primary alcohol. Lanette 22 contains about 70% of $C_{22}$ fatty alcohol, about 20% of $C_{20}$ alcohol, about 9% of $C_{18}$ alcohol, and about 1% of $C_{24}$ fatty alcohol. The weight percentages of these components are shown in Table I below:

TABLE I

| Component | Weight % |
| --- | --- |
| Super White Protopet ® | 70 |
| Behenyl Alcohol | 30 |

B. Preparation of Skin Care Composition Treated Article by Hot Melt Printing

Skin Care Composition A is placed into a heated tank operating at a temperature of 90° C. The composition is subsequently applied with a contact applicator (using a Meltex EP45 hot melt adhesive applicator head operating at a temperature of 90° C.) onto all over the DRI-WEAVE topsheet of Whisper Slim Wing Regular Long manufactured by Procter & Gamble Far East, Inc., at an add-on level=4 g/m² (Treated Article A).

C. Preparation of Barrier Sheet

Barrier Sheet A is made of a paper having basis weight of 40 g/m². The paper is treated with fluoroalkyl ammonium salt made by Minnesota Mining Manufacturing under the name Scotchban FC-807A in the form of solution of water by immersing the paper in the solution then drying. The entirety of one surface of the paper is also treated with silicone such that the surface becomes releasable with adhesive.

D. Application of Barrier Sheet to Skin Care Composition Treated Article

Treated Article A is wrapped by a wrapper comprising a main wrapper sheet, a flap adhesive cover, and a central pad adhesive cover. The flap of Treated Article A is folded onto the topsheet. The flap adhesive cover comprises Barrier Sheet A. The flap adhesive cover is applied to cover the flap adhesive such that the releasable surface of the flap adhesive cover faces the flap adhesive. The central pad adhesive cover comprises Barrier Sheet A. The central adhesive cover is applied to cover the central pad adhesive such that the releasable surface the central pad adhesive cover faces the central pad adhesive. The main wrapper sheet is made of low density polyethylene film having a thickness of 40 μm. The main wrapper sheet, the flap adhesive cover, the central pad adhesive cover are assembled as shown in FIGS. 5-10.

Example 2

A. Preparation of Skin Care Compositions

Skin Care Composition A is prepared in accordance with the description above.

B. Preparation of Skin Care Composition Treated Article by Hot Melt Printing Treated Article A is prepared in accordance with the description above.

C. Preparation of Barrier Sheet

Barrier Sheet B is made of a paper having basis weight of 30 g/m². The paper is treated with Kaolin clay made by Whittaker, Clark and Daniels under the name 2474 Calcined Clay with styrene butadiene rubber based adhesive made by Findley under the name H4031 as the binder by super calendaring. The entirety of one surface of the paper is also treated with silicone such that the surface becomes releasable with adhesive.

D. Application of Barrier Sheet to Skin Care Composition Treated Article

Treated Article A is wrapped by a wrapper comprising a main wrapper sheet, a flap adhesive cover, and a central pad adhesive cover. The flap of Treated Article A is folded onto the topsheet. The flap adhesive cover comprises Barrier Sheet B. The flap adhesive cover is applied to cover the flap adhesive such that the releasable surface of the flap adhesive cover faces the flap adhesive. The central pad adhesive cover comprises Barrier Sheet B. The central pad adhesive cover is applied to cover the central pad adhesive such that the releasable surface of the central pad adhesive cover faces the central pad adhesive. The main wrapper sheet is made of low density polyethylene film having a thickness of 40 μm. The main wrapper sheet, the flap adhesive cover, the central pad adhesive cover are assembled as shown in FIGS. 5-10.

Example 3

A. Preparation of Skin Care Compositions

Skin Care Composition A is prepared in accordance with the description above.

B. Preparation of Skin Care Composition Treated Article by Hot Melt Printing Treated Article A is prepared in accordance with the description above.

C. Preparation of Barrier Sheet

Barrier Sheet C is made of a paper having basis weight of 30 g/m². The paper is treated with polyethylene vinyl acetate made by DuPont under the name ELVAX 40W by extrusion laminating. The entirety of one surface of the paper is also treated with silicone such that the surface becomes releasable with adhesive.

D. Application of Barrier Sheet to Skin Care Composition Treated Article

Treated Article A is wrapped by a wrapper comprising a main wrapper sheet, a flap adhesive cover, and a central pad adhesive cover. The flap of Treated Article A is folded onto the topsheet. The flap adhesive cover comprises Barrier Sheet C. The flap adhesive cover is applied to cover the flap adhesive such that the releasable surface of the flap adhesive cover faces the flap adhesive. The central pad adhesive cover comprises Barrier Sheet C. The central pad adhesive cover is applied to cover the central pad adhesive such that the releasable surface of the central pad adhesive cover faces the central pad adhesive. The main wrapper sheet is made of low density polyethylene film having a thickness of 40 μm. The main wrapper sheet, the flap adhesive cover, the central pad adhesive cover are assembled as shown in FIGS. 5-10.

Example 4

A. Preparation of Skin Care Compositions

Skin Care Composition A is prepared in accordance with the description above.

B. Preparation of Skin Care Composition Treated Article by Hot Melt Printing Treated Article A is prepared in accordance with the description above.

C. Preparation of Barrier Sheet

Barrier Sheet D is made of a low density polyethylene film having a thickness of 40 μm. The film is treated with polyethylene vinyl acetate made by DuPont under the name ELVAX 40W by extrusion laminating. A portion of one surface of the film is treated with silicone such that the surface becomes releasable with adhesive. The rest of the surface of the film is not treated releasably.

D. Application of Barrier Sheet to Skin Care Composition Treated Article

Treated Article A is wrapped by a wrapper comprising a main wrapper sheet, a flap adhesive cover, and a central pad adhesive cover. The flap of Treated Article A is folded onto the topsheet. The flap adhesive cover comprises Barrier Sheet C. The flap adhesive cover is applied to cover the flap adhesive such that the releasable surface of the flap adhesive cover faces the flap adhesive. The main wrapper sheet comprises Barrier Sheet D. The main wrapper sheet is applied to cover the central pad adhesive such that the releasable surface of the central pad adhesive cover faces the central pad adhesive. In this example, the central pad adhesive cover is the release treatment on Barrier Sheet D. The main wrapper sheet and the flap adhesive cover are assembled as shown in FIGS. 5-10. The flap adhesive cover is joined to the portion of the surface of the main wrapper sheet which is not treated releasably.

Example 5

A. Preparation of Skin Care Compositions

An oil-based skin care composition (Skin Care Composition B) is made by mixing the following melted components together: Petrolatum made by Witco Corp. under the name Protopet® 1S, and Behenyl Alcohol made by Henkel Corp. under the name Lanette 22. Protopet® 1S is petrolatum. The ratio of the heavy aliphatic hydrocarbons having alkyl chain length of from 27 to 36 to the light hydrocarbons having alkyl chain length of from 17 to 26 is 2.3:1.0. The ratio of the heavy aliphatic hydrocarbons having alkyl chain length of from 30 to 36 to the light aliphatic hydrocarbons aliphatic having alkyl chain length of from 20 to 26 is 1.7:1.0. The ratio of the heavy aliphatic hydrocarbons having alkyl chain length of from 33 to 36 to the light aliphatic hydrocarbons aliphatic having alkyl chain length of from 23 to 26 is 1.3:1.0. Lanette 22 contains about 70% of $C_{22}$ fatty alcohol, about 20% of $C_{20}$ alcohol, about 9% of $C_{18}$ alcohol, and about 1% of $C_{24}$ fatty alcohol. The weight percentages of these components are shown in Table II below:

TABLE II

| Component | Weight % |
|---|---|
| Protopet ® 1S | 80 |
| Behenyl Alcohol | 20 |

B. Preparation of Skin Care Composition Treated Article by Hot Melt Printing Skin Care Composition B is placed into a heated tank operating at a temperature of 90° C. The composition is subsequently applied with a contact applicator (using a Meltex EP45 hot melt adhesive applicator head operating at a temperature of 90° C.) onto all over the DRI-WEAVE topsheet of Whisper Slim Wing Regular Long manufactured by Procter & Gamble Far East, Inc., in a couple of stripes which are 30 mm wide (lateral direction) and 200 mm long (longitudinal direction) at an add-on level=4 g/m² (Treated Article B).

C. Preparation of Barrier Sheet

Barrier Sheet E is made of a paper having basis weight of 30 g/m². The paper is treated with fumed silica made by Cabot Corp. under the name CAB-O-Sil® TS-720 with styrene butadiene rubber based adhesive made by Findley under the name H4031 as the binder by super calendaring. One surface of the paper is also treated with silicone such that the surface becomes releasable with adhesive.

D. Application of Barrier Sheet to Skin Care Composition Treated Article

Treated Article B is wrapped by a wrapper comprising a main wrapper sheet, a flap adhesive cover, and a central pad adhesive cover. The flap of Treated Article B is folded onto the topsheet. The flap adhesive cover comprises Barrier Sheet E. The flap adhesive cover is applied to cover the flap adhesive such that the releasable surface of the flap adhesive cover faces the flap adhesive. The central pad adhesive cover comprises Barrier Sheet E. The central pad adhesive cover is applied to cover the central pad adhesive such that the releasable surface of the central pad adhesive cover faces the central pad adhesive. The main wrapper sheet is made of low density polyethylene film having a thickness of 40 μm. The main wrapper sheet, the flap adhesive cover, the central pad adhesive cover are assembled as shown in FIGS. 5-10.

Example 6

A. Preparation of Skin Care Compositions

An oil-based skin care composition (Skin Care Composition C) is made by mixing zinc oxide made by Zinc Corporation of America under the name USP-1 and fumed silica made by Cabot Corp. under the name CAB-O-Sil® TS-720 and the following melted components; Petrolatum made by Witco Corp. under the name Super White Protopet®, and Behenyl Alcohol made by Henkel Corp. under the name Lanette 22. These are mixed by a high speed blade mixer (Tokusyu Kika TK Robo Mics, operating at 5000 rpm) at 90° C. Super White Protopet® is petrolatum. The ratio of the heavy aliphatic hydrocarbons having alkyl chain length of from 27 to 36 to the light hydrocarbons having alkyl chain length of from 17 to 26 is 2.3:1.0. The ratio of the heavy aliphatic hydrocarbons having alkyl chain length of from 30 to 36 to the light aliphatic hydrocarbons aliphatic having alkyl chain length of from 20 to 26 is 1.7:1.0. The ratio of the heavy aliphatic hydrocarbons having alkyl chain length of from 33 to 36 to the light aliphatic hydrocarbons aliphatic having alkyl chain length of from 23 to 26 is 1.3:1.0. Lanette 22 contains about 70% of $C_{22}$ fatty alcohol, about 20% of $C_{20}$ alcohol, about 9% of $C_{18}$ alcohol, and about 1% of $C_{24}$ fatty alcohol. USP-1 is zinc oxide having an average particle diameter of about 0.1-1.0 μm. CAB-O-Sil® TS-720 is fumed silica whose surface is treated with polydimethylsiloxane. The weight percentages of the components are shown in Table III below:

TABLE III

| Component | Weight % |
|---|---|
| Super White Protopet ® | 67 |
| Behenyl Alcohol | 30 |
| Fumed Silica | 1.0 |
| Zinc Oxide | 2.0 |

B. Preparation of Skin Care Composition Treated Article by Hot Melt Printing Skin Care Composition C is placed into a heated tank operating at a temperature of 90° C. The composition is subsequently applied with a contact applicator (using a Meltex EP45 hot melt adhesive applicator head operating at a temperature of 90° C.) onto all over the DRI-WEAVE topsheet of Whisper Slim Regular Long (without flaps) manufactured by Procter & Gamble Far East, Inc., at an add-on level=4 g/m² (Treated Article C).

C. Preparation of Barrier Sheet

Barrier Sheet B and D are prepared in accordance with the descriptions above.

D. Application of Barrier Sheet to Skin Care Composition Treated Article

Treated Article C is wrapped by a wrapper comprising a main wrapper sheet, and a topsheet cover. The topsheet cover comprises Barrier Sheet B. The topsheet cover is applied to cover the portion of the topsheet where the skin care composition is applied. The main wrapper sheet comprises Barrier Sheet D. The main wrapper sheet is applied to cover the central pad adhesive such that the releasable surface of the central pad adhesive cover faces the central pad adhesive. The main wrapper sheet and the topsheet cover are assembled as shown in FIG. 11, then folded as shown in FIG. 10.

Example 7

A. Preparation of Skin Care Compositions

Skin Care Composition C is prepared in accordance with the description above.

B. Preparation of Skin Care Composition Treated Article by Hot Melt Printing

Skin Care Composition C is placed into a heated tank operating at a temperature of 90° C. The composition is subsequently applied with a contact applicator (using a Meltex EP45 hot melt adhesive applicator head operating at a temperature of 90° C.) onto all over the DRI-WEAVE topsheet of Whisper Slim Wing Regular Long manufactured by Procter & Gamble Far East, Inc., at an add-on level=4 g/m² (Treated Article D).

C. Preparation of Barrier Sheet

Barrier Sheet B is prepared in accordance with the description above.

D. Application of Barrier Sheet to Skin Care Composition Treated Article

Treated Article D is wrapped by a wrapper comprising a main wrapper sheet, a flap adhesive cover, and a central pad adhesive cover. The flap of Treated Article A is folded onto the topsheet. The flap adhesive cover comprises Barrier Sheet B. The flap adhesive cover is applied to cover the flap adhesive such that the releasable surface of the flap adhesive cover faces the flap adhesive. The central pad adhesive cover comprises Barrier Sheet B. The central pad adhesive cover is applied to cover the central pad adhesive such that the releasable surface of the central pad adhesive cover faces the central pad adhesive. The main wrapper sheet is made of low density polyethylene film having a thickness of 40 µm. The main wrapper sheet, the flap adhesive cover, the central pad adhesive cover are assembled as shown in FIGS. 5-10.

Example 8

A. Preparation of Skin Care Compositions

Skin Care Composition C is prepared in accordance with the description above.

B. Preparation of Skin Care Composition Treated Article by Hot Melt Printing

Treated Article D is prepared in accordance with the description above.

C. Preparation of Barrier Sheet

Barrier Sheet A is made in accordance with the description above.

D. Application of Barrier Sheet to Skin Care Composition Treated Article

Treated Article D is wrapped by a wrapper comprising a main wrapper sheet, a flap adhesive cover, and a central pad adhesive cover. The flap of Treated Article A is folded onto the topsheet. The flap adhesive cover comprises Barrier Sheet A. The flap adhesive cover is applied to cover the flap adhesive such that the releasable surface of the flap adhesive cover faces the flap adhesive. The central pad adhesive cover comprises Barrier Sheet A. The central pad adhesive cover is applied to cover the central pad adhesive such that the releasable surface of the central pad adhesive cover faces the central pad adhesive. The main wrapper sheet is made of low density polyethylene film having a thickness of 40 µm. The main wrapper sheet, the flap adhesive cover, the central pad adhesive cover are assembled as shown in FIGS. 5-10.

Example 9

A. Preparation of Skin Care Composition

An oil-based skin care composition (Skin Care Composition D) is made by mixing the following melted components together: Petrolatum made by Witco Corp. under the name Protopet® 1S, Microcrystalline wax made by Witco Corp. under the name Multiwax® W-835, and Stearyl Alcohol made by the Procter & Gamble Company under the name CO1895. Protopet® 1S is petrolatum. The ratio of the heavy aliphatic hydrocarbons having alkyl chain length of from 27 to 36 to the light hydrocarbons having alkyl chain length of from 17 to 26 is 2.3:1.0. The ratio of the heavy aliphatic hydrocarbons having alkyl chain length of from 30 to 36 to the light aliphatic hydrocarbons aliphatic having alkyl chain length of from 20 to 26 is 1.7:1.0. The ratio of the heavy aliphatic hydrocarbons having alkyl chain length of from 33 to 36 to the light aliphatic hydrocarbons aliphatic having alkyl chain length of from 23 to 26 is 1.3:1.0. Multiwax® W-835 is microcrystalline wax having a consistency of from 60 to 80 at 25° C. measured under ASTM D-1321. CO1895 is a linear $C_{18}$ primary alcohol. The weight percentages of these components are shown in Table IV below:

TABLE IV

| Component | Weight % |
| --- | --- |
| Protopet ® 1S | 80 |
| Microcrystalline Wax | 5 |
| Stearyl Alcohol | 15 |

B. Preparation of Skin Care Composition Treated Article by Hot Melt Spraying

Skin Care Composition D is placed into a heated tank operating at a temperature of 90° C. The composition is subsequently sprayed (using a Dynatec E84B1758 spray head, operating at a temperature of 90° C. and an atomization pressure of 16 kPa) onto the DRI-WEAVE topsheet of Whisper Slim Wing Regular Long manufactured by Procter & Gamble Far East, Inc., at an add-on level=4 g/m² (Treated Article E).

C. Preparation of Barrier Sheet

Barrier Sheet F is made of a paper having basis weight of 30 g/m². The paper is treated with Kaolin clay made by Whittaker, Clark and Daniels under the name 2474 Calcined Clay with polyvinyl alcohol made by Dupont under the name Elvanol 51-05 as the binder by painting with a roller. One surface of the paper is also treated with silicone such that the surface becomes releasable with adhesive.

D. Application of Barrier Sheet to Skin Care Composition Treated Article

Treated Article E is wrapped by a wrapper comprising a main wrapper sheet, a flap adhesive cover, and a central pad adhesive cover. The flap of Treated Article D is folded onto the topsheet. The flap adhesive cover comprises Barrier Sheet F. The flap adhesive cover is applied to cover the flap adhesive such that the releasable surface of the flap adhesive cover faces the flap adhesive. The central pad adhesive cover comprises Barrier Sheet F. The central pad adhesive cover is applied to cover the central pad adhesive such that the releasable surface of the central pad adhesive cover faces the central pad adhesive. The main wrapper sheet is made of low density polyethylene film having a thickness of 40 µm. The main wrapper sheet, the flap adhesive cover, the central pad adhesive cover are assembled as shown in FIGS. 5-10.

Example 10

A. Preparation of Skin Care Compositions

Skin Care Composition D is prepared in accordance with the description above.

B. Preparation of Skin Care Composition Treated Article by Hot Melt Printing Treated Article E is prepared in accordance with the description above.

C. Preparation of Barrier Sheet

Barrier Sheet B and C are made in accordance with the descriptions above.

D. Application of Barrier Sheet to Skin Care Composition Treated Article

Treated Article D is wrapped by a wrapper comprising a main wrapper sheet, a flap adhesive cover, and a central pad adhesive cover. The flap of Treated Article A is folded onto the topsheet. The flap adhesive cover comprises Barrier Sheet C. The flap adhesive cover is applied to cover the flap adhesive such that the releasable surface of the flap adhesive cover faces the flap adhesive. The central pad adhesive cover comprises Barrier Sheet B. The central pad adhesive cover is applied to cover the central pad adhesive such that the releasable surface of the central pad adhesive cover faces the central pad adhesive. The main wrapper sheet is made of low density polyethylene film having a thickness of 40 µm. The main wrapper sheet, the flap adhesive cover, the central pad adhesive cover are assembled as shown in FIGS. 5-10.

It should also be understood that all of the limits and ranges specified herein include all narrower ranges, limits, and amounts that are within the specified limits and ranges and that such narrower ranges and limits may be claimed even though those limits and ranges are not separately listed.

While particular embodiments of the present invention have been illustrated and described, it would be obvious to those skilled in the art that various other changes and modifications can be made without departing from the spirit and scope of the invention.

What is claimed is:

1. An absorbent article comprising a pair of longitudinal side edges, a liquid pervious topsheet, a liquid impervious backsheet joined to said topsheet, and an absorbent core positioned between said topsheet and said backsheet, said absorbent article comprising:
    an oil-based skin care composition provided on at least a portion of said topsheet,
    a flap extending laterally outwardly from each longitudinal side edge, said flap comprising a garment surface, said garment surface of said flap comprising a flap adhesive, and
    a barrier sheet comprising a base sheet attached only to said absorbent article by said flap adhesive, wherein said barrier sheet reduces the migration of the skin care composition therethrough to protect said flap adhesive from said oil-based skin care composition, the base sheet comprising a component selected from the group consisting of fluorochemicals, hydrophilic polymers, inorganic particles, and mixtures thereof; and
    wherein the flaps are folded over the body surface of the absorbent article and the barrier sheet covers the adhesive before use of the absorbent article.

2. The absorbent article of claim 1 wherein at least one surface of the barrier sheet is treated so as to be releasable.

3. An absorbent article comprising a pair of longitudinal side edges, a liquid pervious topsheet, a liquid impervious backsheet joined to said topsheet, and an absorbent core positioned between said topsheet and said backsheet, said absorbent article comprising:
    an oil-based skin care composition provided on at least a portion of said topsheet,
    a flap extending laterally outwardly from each longitudinal side edge, said flap comprising a garment surface, said garment surface of said flap comprising a flap adhesive, and
    a barrier sheet that only covers a portion of the absorbent article that is the garment surface of the flap, wherein said barrier sheet reduces the migration of the skin care composition therethrough to protect said flap adhesive from said oil-based skin care composition, the barrier sheet comprising a component selected from the group consisting of fluorochemicals, hydrophilic polymers, inorganic particles, and mixtures thereof; and
    wherein the flaps are folded over the body surface of the absorbent article and the barrier sheet covers the adhesive, provides a connection between each flap, and keeps the flaps in the desired flap position before use of the absorbent article.

4. An absorbent article comprising a pair of longitudinal side edges, a liquid pervious topsheet, a liquid impervious backsheet joined to said topsheet, and an absorbent core positioned between said topsheet and said backsheet, said absorbent article comprising:
    an oil-based skin care composition provided on at least a portion of said topsheet,
    a flap extending laterally outwardly from each longitudinal side edge, said flap comprising a garment surface, said garment surface of said flap comprising a flap adhesive, and
    a barrier sheet to reduce the migration of the oil-based skin care composition therethrough, wherein the barrier sheet is disposed to directly cover a position of the absorbent article which is not desired to be exposed to the skin care composition, and wherein the barrier sheet comprises a base sheet wherein the base sheet is treated with a composition comprising a component selected from the group consisting of fluorochemicals, hydrophilic polymers, inorganic particles, or mixtures thereof.

5. The absorbent article of claim 1, wherein both sides of the base sheet are treated with a component selected from the group consisting of fluorochemicals, hydrophilic polymers, inorganic particles, and mixtures thereof.

6. The absorbent article of claim 5, wherein the barrier sheet provides a connection between each flap, keeping the flaps in the desired flap position before use.

* * * * *